(12) United States Patent
Deschamps et al.

(10) Patent No.: US 9,222,913 B2
(45) Date of Patent: Dec. 29, 2015

(54) ANALYSIS AND ASSAY OF GLYCATED HAEMOGLOBINS BY CAPILLARY ELECTROPHORESIS, BUFFER COMPOSITIONS AND KITS FOR CAPILLARY ELECTROPHORESIS

(75) Inventors: Gérald Deschamps, Ury (FR); Frédéric Robert, Mennecy (FR); Denis Simonin, Evry (FR)

(73) Assignee: SEBIA, Lisses (FR)

( * ) Notice: Subject to any disclaimer, the term of this patent is extended or adjusted under 35 U.S.C. 154(b) by 199 days.

(21) Appl. No.: 12/827,795

(22) Filed: Jun. 30, 2010

(65) Prior Publication Data

US 2011/0000788 A1    Jan. 6, 2011

(30) Foreign Application Priority Data

Jul. 1, 2009 (FR) ...................................... 09 03220

(51) Int. Cl.
   *G01N 27/447* (2006.01)
(52) U.S. Cl.
   CPC ................................. *G01N 27/44747* (2013.01)
(58) Field of Classification Search
   CPC ................ G01N 27/26; G01N 27/447; G01N 27/44747; C07F 5/02
   USPC ..................... 204/450–468, 600–616
   See application file for complete search history.

(56) References Cited

U.S. PATENT DOCUMENTS 4,861,728 A * 8/1989 Wagner .......................... 436/501
5,120,413 A * 6/1992 Chen et al. .................... 204/451

(Continued)

FOREIGN PATENT DOCUMENTS

EP    1 659 398 A1    5/2006
JP    6-502244          3/1994

(Continued)

OTHER PUBLICATIONS

Margo P. Cohen, Rex S. Clements, Measuring Glycated Proteins: Clinical and Methodological Aspects, Diabetes Technology & Therapeutics, vol. 1, No. 1, pp. 57-70 (1996).*

(Continued)

*Primary Examiner* — J. Christopher Ball
*Assistant Examiner* — Maris R Kessel
(74) *Attorney, Agent, or Firm* — Birch, Stewart, Kolasch & Birch, LLP

(57) ABSTRACT

The invention relates to a method for analysis by capillary electrophoresis of glycated haemoglobins comprising at least one globin chain comprising a glucose residue bound to the amino acid in the N-terminal position, contained in a biological sample, said method comprising using a buffer composition comprising at least one compound which is capable of specifically complexing glucose residues of one or several glycated haemoglobin(s) and of providing said glycated haemoglobin(s) with several negative electric charges at an alkaline pH. By way of example this compound may be 3,4- or 3,5-dicarboxyphenylboronic acid, preferably 3,5-dicarboxyphenylboronic acid. Said method may in particular be used to separate and assay haemoglobin $HbA_{1c}$ present in a biological sample optionally comprising other haemoglobins, in particular other minor fractions. The invention also concerns buffer compositions for use in said analysis, as well as kits for the analysis and for the assay of glycated haemoglobins by capillary electrophoresis.

15 Claims, 16 Drawing Sheets

(56) References Cited

U.S. PATENT DOCUMENTS

| | | | |
|---|---|---|---|
| 5,599,433 A * | 2/1997 | Keo et al. | ............ 204/451 |
| 5,631,364 A | 5/1997 | Sundrehagen et al. | |
| 2002/0173044 A1 | 11/2002 | Pachl et al. | |
| 2010/0187110 A1 | 7/2010 | Tanaka et al. | |

FOREIGN PATENT DOCUMENTS

| | | |
|---|---|---|
| WO | WO 92/08984 | 5/1992 |
| WO | WO 96/22524 A1 | 7/1996 |
| WO | WO 98/40750 A1 | 9/1998 |
| WO | WO 2008/029685 A1 | 3/2008 |
| WO | WO 2008/029885 A1 | 3/2008 |

OTHER PUBLICATIONS

French Preliminary Search Report mailed on Feb. 9, 2010 for the corresponding Priority French application No. 0903220.

Song et al., Sensors and Actuators B: Chemical, "Boronic acid-modified thin film interface for specific binding of glycated hemoglobin (HbA1c) and electrochemical biosensing", vol. 140, pp. 233-239, (2009).

Chen et al., "Practical Method for the Synthesis of Substituted Phenylboronic Acids", Journal of Sichuan Normal University (Natural Science), vol. 23, No. 5 (2000) pp. 511-512.

Hall, D.G., Boronic Acids: Preparation and Applications in Organic Synthesis and Medicine (e.d. D.G. Hall), Wiley-VCH Verlag GmbH & Co. KGaA, Weinheim, FRG. doi: 10.1002/3527606548.ch1, pp. 1-57 and 79-80 only.

Menard et al., "Quantitative Determination of Glycosolated Hemoglobin A1 by Agar Gel Electrophoresis", Clin. Chem, vol. 26, No. 11 (1980) pp. 1598-1602.

* cited by examiner

| [3,5-dCPBA] | Δt = t A$_{1c}$ - t A$_0$ (min) | Δt/t = [t A$_{1c}$ - t A$_0$] / t A$_0$ | t A$_0$ (min) |
|---|---|---|---|
| 0 | 0 | 0 | 18.042 |
| 10 | 0.918 | 0.050 | 18.316 |
| 20 | 1.757 | 0.093 | 18.96 |
| 30 | 2.018 | 0.104 | 19.341 |
| 30 | 1.979 | 0.105 | 18.927 |
| 40 | 2.264 | 0.116 | 19.502 |
| 50 | 2.546 | 0.127 | 19.991 |
| 60 | 2.885 | 0.139 | 20.699 |
| 70 | 3.04 | 0.143 | 21.218 |
| 80 | 3.224 | 0.149 | 21.688 |
| 90 | 3.56 | 0.158 | 22.495 |
| 100 | 3.998 | 0.172 | 23.249 |
| 120 | 4.568 | 0.187 | 24.478 |

| Sample | % A$_{1c}$ - HPLC | Gross values % A$_{1c}$ - EC | Corrected values %A$_{1c}$ - EC | HPLC – corrected EC |
|---|---|---|---|---|
| 1 | 5.5 | 3.9 | 5.3 | 0.2 |
| 2 | 6.9 | 5.5 | 6.7 | 0.2 |
| 3 | 7.1 | 6.1 | 7.1 | 0.0 |
| 4 | 8.9 | 8.4 | 8.7 | 0.2 |
| 5 | 6.6 | 5.5 | 6.8 | -0.2 |
| 6 | 8.3 | 7.3 | 8.4 | -0.1 |
| 7 | 5.1 | 4.1 | 5.4 | -0.3 |
| 8 | 6.4 | 5.2 | 6.5 | -0.1 |
| 9 | 6.5 | 4.9 | 6.2 | 0.3 |
| 10 | 6.1 | 4.7 | 6.0 | 0.1 |
| 11 | 5.2 | 3.6 | 5.3 | -0.1 |
| 12 | 12.7 | 13.3 | 12.5 | 0.2 |
| 13 | 6.4 | 5.5 | 6.6 | -0.2 |
| 14 | 6.5 | 5.0 | 6.3 | 0.2 |
| 15 | 7.0 | 5.8 | 6.8 | 0.2 |
| 16 | 9.4 | 8.9 | 9.0 | 0.4 |
| 17 | 5.3 | 3.9 | 5.5 | -0.2 |
| 18 | 7.5 | 6.2 | 7.5 | 0.0 |
| 19 | 6.2 | 4.7 | 6.1 | 0.1 |
| 20 | 6.8 | 5.7 | 6.8 | 0.0 |
| 21 | 7.9 | 7.1 | 7.9 | 0.0 |
| 22 | 9.3 | 8.9 | 9.2 | 0.1 |
| 23 | 5.2 | 3.8 | 5.3 | -0.1 |
| 24 | 8.3 | 7.4 | 8.3 | 0.0 |
| 25 | 8.0 | 6.9 | 8.1 | -0.1 |
| 26 | 8.9 | 8.2 | 8.8 | 0.1 |
| 27 | 6.3 | 5.1 | 6.3 | 0.0 |
| 28 | 6.1 | 4.6 | 6.0 | 0.1 |
| 29 | 7.6 | 6.6 | 7.5 | 0.1 |
| 30 | 8.8 | 8.1 | 8.5 | 0.3 |
| 31 | 7.7 | 6.7 | 7.7 | 0.0 |

HYDRAGEL 15 Hb A1c 1  2  3  4  5  6  7  8  9

| Glucose Concentration (g/L) | % A1c gel | % A1c EC |
|---|---|---|
| 0 (reference) | 4.1 | 4.2 |
| 1 | 4.5 | - |
| 5 | 4.6 | 4.3 |
| 10 | 5.3 | 4.3 |
| 20 | 7.8 | 4.1 |
| 30 | 8.6 | 4.1 |
| 50 | 14.8 | 4.1 |

ANALYSIS AND ASSAY OF GLYCATED HAEMOGLOBINS BY CAPILLARY ELECTROPHORESIS, BUFFER COMPOSITIONS AND KITS FOR CAPILLARY ELECTROPHORESIS

The present application concerns the field of the analysis and assay of glycated haemoglobins, in particular haemoglobin $A_{1c}$, by capillary electrophoresis.

The invention pertains to a method for analysis by capillary electrophoresis of a biological sample comprising one or several haemoglobin(s) and in particular one or several glycated haemoglobin(s), as well as appropriate buffer compositions for said analysis, and kits for analysis and for assay of glycated haemoglobins by capillary electrophoresis.

Haemoglobin (Hb) is a globular molecule generally comprising four sub-units each constituted by a polypeptide chain conjugated to a heme portion. The polypeptide chains are collectively designated by the name "globin portion" of the haemoglobin molecule.

All human haemoglobins are constituted by four polypeptide chains in two groups of two identical chains. In an adult human, three types of haemoglobin are normally present: haemoglobin A (HbA), which is the vast majority (it generally represents approximately 97% of the haemoglobin in an adult), constituted by 2 alpha chains and two beta chains (haemoglobin $\alpha_2\beta_2$), haemoglobin A2 (HbA2, which generally represents approximately 1-3% of the haemoglobin in an adult) constituted by two alpha chains and two delta chains (haemoglobin $\alpha_2\delta_2$), and foetal haemoglobin (HbF), constituted by two alpha chains and two gamma chains (haemoglobin $\alpha_2\gamma_2$), which only subsists in trace amounts (generally less than 1% of the haemoglobin in an adult) and remains limited to a restricted cell population ("F cells").

Haemoglobin contains species known as minor species; they are glycated haemoglobins.

Glycated haemoglobin (also known as glycosylated haemoglobin or glycohaemoglobin) corresponds to the set of haemoglobin molecules modified by binding of oses, principally glucose, on the amine functions ($NH_2$) of the globin; the $NH_2$ group of a haemoglobin condenses with an aldehyde group derived from a reducing sugar. This reaction, which is non-enzymatic, is then stabilized by an Amadori rearrangement. Potential glycation sites are the N-terminal amino acids of the four globin chains of haemoglobin ($\alpha$ chains and $\beta$, $\delta$, or $\gamma$ chains depending on the type of haemoglobin) and the free amino-epsilon groups (in particular those of the lysine residues) in the globin chains of the haemoglobin.

Many forms of glycated haemoglobin exist; they depend on the number of bound oses, the nature of the globin chains and the oses bound on said chains and on the position of said oses on the globin chains.

The term "total glycated haemoglobin" is used when considering the molecules of glycated haemoglobin on any $NH_2$ residue.

The term "haemoglobin A1 (HbA1)" is reserved for molecules of haemoglobin A having one molecule of ose bound to the N-terminal amino acid of one or two beta chains of the protein. The A1 fraction, which is heterogeneous, comprises in particular the minor fractions $A_{1a}$, $A_{1b}$ and especially $A_{1c}$. Haemoglobin $A_{1a}$ (Hb$A_{1a}$) includes haemoglobin $A_{1a1}$ (Hb$A_{1a1}$), in which the ose bound to the N-terminal amino acid is fructose 1-6 diphosphate, and haemoglobin $A_{1a2}$ (Hb$A_{1a2}$), in which the ose bound to the N-terminal amino acid is glucose-6-phosphate. In the case of haemoglobin $A_{1b}$ (Hb$A_{1b}$), the ose bound to the N-terminal amino acid is pyruvate. Finally, the ose bound to the N-terminal amino acid of the beta chains of haemoglobin $A_{1c}$ (Hb$A_{1c}$) is glucose; Hb$A_{1c}$ is obtained by condensation of one molecule of glucose with the $NH_2$ group of the N-terminal valine of the $\beta$ chain, to form a stable keto-amine, derived from a rearrangement (Amadori rearrangement) of a previously formed unstable aldimine (designated as labile Hb$A_{1c}$ or preA$_{1c}$).

Finally, the term haemoglobin $A_0$ (Hb$A_0$) generally encompasses non-glycated A haemoglobins and glycated A haemoglobins not comprising an ose bound to the amino acid in the N-terminal position of the $\beta$ chains.

Protein glycation (including glycated haemoglobin and in particular haemoglobin $A_{1c}$, among many others) is caused by a too high concentration of sugars in the blood (as is the case with diabetes). The glycation of proteins alters their functions, causing cell lesions, tissue lesions and vascular ageing, and participates in the development of several diseases such as arteriosclerosis, renal insufficiency, diabetic retinopathy and cataracts. Once glycated, haemoglobin transports oxygen less well.

Included among all of the groups and sub-groups of haemoglobin, Hb$A_{1c}$ is of particular interest as it serves as a long-lasting marker of the diabetic state of patients. The formation of Hb$A_{1c}$ is dependent on glycaemia (concentration of glucose in the blood). It intervenes throughout the lifespan of the red blood cells, which is normally 120 days. The blood concentration of Hb$A_{1c}$ thus indicates the average glycaemia over the 2-3 months preceding assay. Elevation of the blood concentration of Hb$A_{1c}$ is indicative of prolonged hyperglycaemia during that period. The blood concentration of Hb$A_{1c}$ is not influenced by short-term fluctuations in the levels of blood glucose. Thus, by measuring the Hb$A_{1c}$ level between two dates, the evolution of diabetes can be monitored.

In a diabetic patient, the aim is to obtain a Hb$A_{1c}$ level that is as close as possible to the figures characterizing a good balance of glycaemia. The reference value in a non-diabetic human with a normal glycaemia is 4% to 6% Hb$A_{1c}$ in the blood compared with the total concentration of A haemoglobins (glycated haemoglobins and non-glycated haemoglobins) (i.e. 20 to 42 mmol/moles; Panteghini et al, 2007).

The detection of glycated haemoglobins, in particular the detection of an increase in the Hb$A_{1c}$ level, is thus of manifest interest for the diagnosis of diabetes (type 1 or type 2) or monitoring diabetic patients, in particular to evaluate the efficacy of a treatment against diabetes (type 1 or type 2).

However, interpreting the results may occasionally be difficult, since many factors may falsify the results, in particular the presence of abnormal haemoglobins.

Indeed, haemoglobins termed "abnormal" or variant, in particular denoted by the letters S, C, D, E, H and J, are encountered in certain patients. Haemoglobin A is partially or completely replaced by one or several abnormal haemoglobins. They originate in particular from reduced synthesis of certain globin chains and/or from a modification of the structure of the $\alpha$, $\beta$, $\gamma$ or $\delta$ chains, by substitution of one amino acid by another. Thus, a modification in the $\beta$ chain may, for example, give rise to S or C haemoglobins ($\alpha_2\beta_2$ haemoglobins in which the glutamic acid in position 6 in the $\beta$ chain is respectively substituted by a valine or a lysine).

These abnormal haemoglobins are also susceptible to glycation. Thus, haemoglobins $S_{1c}$ (Hb$S_{1c}$) and $C_{1c}$ (Hb$C_{1c}$) exist which, like Hb$A_{1c}$, comprise one molecule of glucose bound to the N-terminal valine on the $\beta$ chains (Abraham et al, 1984).

Methods for analysis and assay of glycated haemoglobin and in particular haemoglobin Hb$A_{1c}$ may be classified into 2 broad categories.

The first category, the major category, includes methods such as immunoassay or affinity chromatography. It is based on the structural characteristics of the sugar molecule bound to the haemoglobin. As an example, the publication by Wilson et al, 1993 and U.S. Pat. No. 6,162,645 describe a method for the assay of glycated haemoglobin found in a sample of human blood by affinity chromatography. Said method is based on the use of a solid positively charge phase, coupled via a polyanionic compound (for example polyacrylic acid), to boronic acid, phenylboronic acid, boric acid or a similar boronate compound. When a blood sample to be analyzed is incubated with that solid phase, the glucose residues of the glycated haemoglobin molecules present in that sample are complexed with the boronate compound. The glycated haemoglobin molecules are thus grafted onto the solid phase. The proportion of glycated haemoglobin immobilized on the solid phase compared with the proportion of non-immobilized haemoglobin can then be quantified. That assay is carried out either by measuring the extinction of fluorescence (Wilson et al, 1993), or by using labelled antibodies directed against human haemoglobin (U.S. Pat. No. 6,162,645).

The second category of methods for the analysis and assay of glycated haemoglobin includes ion exchange chromatography or electrophoresis. It exploits the physico-chemical characteristics of the molecules and is based on the charge difference existing between glycated proteins and non-glycated proteins.

Of the various analytical methods allowing glycated haemoglobin to be assayed that are described in the literature, electrophoretic methods are divided into several categories: gel analyses include the polyacrylamide gel isoelectric focusing analysis (Beccaria, 1978; Simon, 1982; Stickland, 1982; Bosisio, 1994) and agarose gel analysis (U.S. Pat. Nos. 5,246,558; 4,222,836; Menard, 1980). Capillary electrophoresis analyses include isoelectric focusing analysis (Molteni, 1994; Hempe, 1994), free solution analysis using an anti-$A_{1c}$ antibody (U.S. Pat. No. 5,431,793), free solution analysis using a naked capillary (U.S. Pat. No. 5,599,433) and free solution analysis using a dynamic coating (EP 0 733 900 A2; U.S. Pat. No. 5,611,903).

Analysis by electrophoresis of a biological sample can separate the various proteins present in the sample, in particular the various haemoglobins, and enables determination of the quantity and/or proportion of one or several protein(s) of interest in the biological sample. In capillary electrophoresis, in a capillary filled with an electrolyte, the proteins of a biological sample migrate under the effect of an electric field from the anode towards the cathode as a function of their mass and their charge. They thus produce an electrophoretic migration profile comprising a series of peaks (also termed fractions), each of them corresponding to one or several proteins. Abnormal haemoglobins such as HbS, HbC and HbE have a different electrophoretic mobility from that of HbA. Further, because of the ose residue bound to the N-terminal amino acid of the beta chains, the $HbA_1$ has a reduced isoelectric point and, as a result, an electric charge that is slightly different from that of the other $HbA_0$ type haemoglobins. Thus, in an electrophoretic field or in an ion exchange resin, the migration rate of $HbA_1$ is different from that of $HbA_0$, which enables separating $HbA_1$ from $HbA_0$, which has a different charge.

The advantage of capillary electrophoresis also resides in the fact that only very small quantities of the biological sample to be analyzed are necessary. Further, separation by this technique may be very rapid, since high voltages can be used without causing the sample to heat up too much during separation.

Analysis by isoelectric focussing (Molteni, 1994; Hempe, 1994) is carried out in coated capillaries. Methylcellulose is used for the coating. The catholyte used is sodium hydroxide (NaOH) and the anolyte is phosphoric acid ($H_3PO_4$). By using ampholytes, this analysis enables separation of various variants of haemoglobin, including $HbA_{1c}$, the peak of which is very close to that of HbA ($\Delta pI<0.10$). Although this method functions well, it is not simple to carry out routinely and necessitates great precision, in particular as regards the pH range of the ampholytes (the isoelectric point (pI) of $HbA_{1c}$ is very close to that of $HbA_0$).

Free solution analysis using an anti-$HbA_{1c}$ antibody (U.S. Pat. No. 5,431,793) is carried out in a borate buffer at a basic pH (pH of 8 to 10), using samples subjected to a reaction with a anti-$HbA_{1c}$ monoclonal antibody. More precisely, a first electropherogram is produced using the working sample without prior reaction with an anti-$HbA_{1c}$ antibody. A single peak is obtained, with area x, containing all of the haemoglobins (including $HbA_{1c}$). A second electropherogram is obtained by analyzing the working sample which has been brought into contact with the anti-$HbA_{1c}$ antibody. The non-bound anti-$HbA_{1c}$ antibody, the anti-$HbA_{1c}$ antibody/$HbA_{1c}$ complex and the haemoglobins not complexed by the antibody are thus separated. The quantity of $HbA_{1c}$ is then determined by the difference of the area under the peaks between the peak for the first electropherogram and that of the second relative to the haemoglobins not complexed by the anti-$HbA_{1c}$ antibody, with area y, i.e. a quantity x-y. This method thus proves to be long and complicated in implementation.

The free solution analysis method using a naked capillary (U.S. Pat. No. 5,599,433) involves a sugar complexing agent bound to haemoglobin (borate) and a zwitterionic buffer (CAPS) at a basic pH (pH of 9 to 12). The profile obtained (shown in FIG. 1 of the present application) under the conditions described show a rather small separation of the peaks for $HbA_1$ (described as being the peak for $HbA_{1c}$ in patent U.S. Pat. No. 5,599,433) and $HbA_0$ (see Example 1). Further, analysis of the purified minor fractions shows that the $HbA_{1a,b}$ fractions co-migrate with $HbA_{1c}$, interfering with the final assay result (see Example 2 and FIG. 2 of the present application). In fact, that technique separates the $HbA_0$ and $HbA_1$ fractions, but does not separate the $HbA_1$ fractions themselves.

The technique for capillary analysis with a dynamic double coating (EP 0 733 900 A2; U.S. Pat. No. 5,611,903) is used in the only test based on capillary electrophoresis which is commercially available (Analis CEofix™ $HbA_{1c}$ kit). It consists of a first wash of the capillary with an "initiator" containing a polycation (in solution, pH 4.6) resulting in coating the wall of the capillary with said polycation. A second wash is then carried out with the analysis buffer containing a polyanion (pH 4.6), which has the effect of providing a second coating layer by interaction with the polycation. The quantity of negative electrical charges then present on the internal wall of the capillary is even higher than with a naked capillary, resulting in a much higher electroosmotic flux. The resolution obtained between the various forms of haemoglobin analyzed (including glycated Al haemoglobins) is satisfactory, with short analysis times. From a practical viewpoint, this double coat must be re-applied between each analysis using a precise procedure provided by the kit's manufacturer but which is only described for a mono-capillary apparatus ((P/ACE, Beckman) not adapted to routine analyses.

Thus, there is a need for reagents and a simple method of implementation that can effectively separate glycated haemoglobins, in particular $HbA_{1c}$, from other haemoglobins, variants, interfering forms (labile forms, acetylated forms, carbamylated forms) and from other minor fractions (especially $HbA_{1a}$ and $HbA_{1b}$) present in a biological sample containing other haemoglobins. Ideally, such a method can produce a semi-quantitative or quantitative assay of glycated haemoglobins, in particular of $HbA_{1c}$, directly from the electrophoretic profile obtained.

The present invention proposes an alternative capillary electrophoresis method, which enables performing a semi-quantitative or quantitative analysis of one or several glycated haemoglobin(s) comprising at least one globin chain comprising a glucose residue bound to the amino acid in the N-terminal position, contained in a biological sample in particular comprising other haemoglobins (glycated and/or non-glycated). Said method of the invention exploits both the structural characteristics of the glucose molecules bound to said glycated haemoglobins and the charge differences existing between the various haemoglobins of the sample.

The inventors have shown that by using a particular buffer composition, it is possible to obtain greatly improved separation of glycated haemoglobin(s) comprising a glucose residue bound to the amino acid in the N-terminal position on at least one globin chain, and in particular on the beta chains, and more particularly a greatly improved separation of $HbA_{1c}$.

One of the advantages of the method of the invention is that because said buffer composition is used, the electrophoresis peak corresponding to one or several types of glycated haemoglobin(s) of interest (one or several types of haemoglobin(s) comprising a glucose residue bound to the amino acid in the N-terminal position on at least one globin chain, for example $HbA_{1c}$) is displaced, when it is present in a biological sample, with respect to the position of the peak which would be obtained without the buffer composition. This displacement does not interfere with the separation of the other proteins, in particular the other haemoglobins (glycated and/or non-glycated) of the sample. This in particular enables separation of $HbA_{1c}$ from other minor $HbA_1$ (in particular $HbA_{1a}$ and $HbA_{1b}$). As a consequence, means that the results of the analysis can be read reliably and allows the accurate assay of one or several glycated haemoglobin(s) of interest comprising one or several glucose residue(s) with one glucose bound to the amino acid in the N-terminal position of at least one globin chain (for example haemoglobin $A_{1c}$).

The method of the invention thus constitutes a method of choice with a view to establishing a diagnosis or of monitoring diabetic patients, in particular to evaluate the effectiveness of an anti-diabetic treatment.

Thus, the present application provides a method for analysis, by capillary electrophoresis, of glycated haemoglobins (one or several glycated haemoglobin(s)) comprising one or several glucose residue(s) contained in a biological sample comprising one or several haemoglobin(s), said method comprising using a buffer composition comprising at least one compound which is capable of specifically complexing glucose residues (one or several residue(s)) of glycated haemoglobins (one or several glycated haemoglobin(s)) of the biological sample and also of providing said glycated haemoglobins with several negative electrical charge(s) at an alkaline pH (i.e. a pH of more than 7).

The term "several" as used in the context of the present application means at least two, i.e. two or more than two, for example, two, three, four, five, six, seven, eight, nine, ten or more than ten.

The term "at least one" as used in the context of the present application means one or several.

The term "haemoglobin" as used in the context of the present application means any form or fraction of haemoglobin (including the minor fractions), whether they be normal or abnormal, as well as the many variants of said haemoglobins (at least 1000 variants of haemoglobin have been described).

The term "glycated haemoglobin" as used in the context of the present application means any haemoglobin modified by binding one or several sugar(s), in particular one or several glucose, glucose-6-phosphate, fructose 1-6 diphosphate or pyruvate, to one or several globin chain(s) (whatever the globin chain). The sugar(s) may be bound to the amino acid in the N-terminal position on a globin chain and/or to an amino acid with a free amino acid group (for example lysine).

The term "globin chain" as used in the present application means any globin chain known to the skilled person, in particular a chain selected from alpha ($\alpha$), beta ($\beta$), delta ($\delta$) and gamma ($\gamma$) chains, whether normal or abnormal, or a variant of one of said chains. According to a particular embodiment, said "globin chain" is a beta chain, for example a beta chain of a $A_1$ haemoglobin, in particular $A_{1c}$, S or C.

When reference is made in the embodiments of the invention to "glycated haemoglobin", it should be understood that said embodiments are of particular application to each particular type of glycated haemoglobin cited in the present application.

Unless otherwise indicated, each embodiment indicated in this application is applicable independently of and/or in combination with any or several of the other described embodiments.

The capillary electrophoresis analysis method of the invention is applicable to a biological sample comprising at least one glycated haemoglobin comprising one or several glucose residue(s) and necessarily comprising, on one or several globin chain(s) and in particular on the beta chains, a glucose residue bound to the amino acid in the N-terminal position. These haemoglobins are designated as "haemoglobins glycated in the N-terminal position" in the present application.

Said method enables separation of one or several haemoglobins glycated in the N-terminal position from other glycated haemoglobins (i.e. glycated haemoglobins wherein the globin chains are devoid of a glucose residue bound to the amino acid in the N-terminal position) or from non-glycated haemoglobins, which may be present in the analyzed biological sample.

According to a particular embodiment, the amino acid in the N-terminal position on the beta chain(s) is valine.

In a preferred embodiment, the analysis method of the invention is intended for the analysis of a biological sample comprising haemoglobin $A_{1c}$. In particular, it is appropriate for separating haemoglobin $A_{1c}$ from other haemoglobins or from the other haemoglobins (differently glycated or non-glycated) which may be present in the analyzed biological sample, and in particular from other minor fractions, for example $HbA_{1a}$ and from $HbA_{1b}$.

According to a particular embodiment, the analysis method of the invention can separate haemoglobin $S_{1c}$ and/or haemoglobin $C_{1c}$ from the other haemoglobins (differently glycated or non-glycated) which may be present in the analyzed biological sample.

The term "buffer composition" means a composition, in particular a solution, which retains approximately the same pH despite the addition of small quantities of an acid or a base or despite dilution.

The term "to complex" or "complexing" is used in the present application to signify that an association (chemical or simply physical) occurs between two entities, in particular between two molecules (for example a small molecule and a macromolecule) via functional groups.

In a preferred embodiment, one of these two entities (the compound which is capable of complexing glucose residues) combines with (for example reacts with) a cis-diol group, in particular with two vicinal hydroxyl groups of a glucose residue from the other entity (a glycated haemoglobin).

As can be seen in the "examples" section, "specifically complexing the glucose residue(s) of one or several glycated haemoglobin(s) and providing said glycated haemoglobin(s) with negative charges at an alkaline pH" in the present application means that the compound used in the context of the present invention allows to displace the electrophoretic migration peak corresponding to a haemoglobin glycated in the N-terminal position by glucose, beyond the electrophoretic migration zone corresponding to haemoglobins glycated in the N-terminal position by another sugar (for example glucose-6-phosphate, fructose 1-6 di-phosphate, or pyruvate), and preferably outside the zone of the electrophoretic migration peaks corresponding to other haemoglobins of the sample. Thus, the minor fractions which do not comprise any glucose residue bond to the N-terminal amino acid of the beta chains, in particular the $A_{1a}$ and $A_{1b}$ fractions, do not interfere with the analysis of the $HbA_{1c}$ according to the method of the invention.

As an example, the capacity of a compound to specifically complex glucose residues of one or several glycated haemoglobin(s) and to provide negative charges at an alkaline pH in the context of the invention may be demonstrated using the following test: a reference sample (for example "$HbA_{1a}$, $HbA_{1b}$ mixture", "$A_{1c}$" and "$A_0$" from Exocell, USA), containing various purified fractions of glycated haemoglobin and in particular the $A_0$ and $A_{1c}$ fractions or the $A_0$, $A_{1b}$ and $A_{1a}$, fractions, is introduced into a capillary electrophoresis capillary containing the following buffer composition: 200 mM of CHES, 20 mM of putrescine, between 10 and 120 mM (for example 30 mM or 50 mM) of test compound, if necessary 2.5 g/l of sodium chloride, water, and if necessary, a base to adjust the pH to a value greater than 9, for example 9.4. Naked capillary free solution capillary electrophoresis is then carried out, for example using a Capillaries® (Sebia) apparatus, at a wavelength of 415 nm. Next, the electrophoretic profile obtained is studied; if the separation between the peak corresponding to $HbA_{1c}$ and the peak corresponding to $HbA_0$ (or, depending on the type of sample used, between the peak corresponding to $HbA_{1c}$ and the peaks corresponding to $HbA_0$, $HbA_{1b}$ and $HbA_{1a}$) is complete, then the test compound is considered to be capable of specifically complexing glucose residues and of providing negative charges at an alkaline pH in the sense of the invention. In contrast, if the peak corresponding to $HbA_{1c}$ and that which corresponds to $HbA_{1b}$ (or, depending on the type of sample used, the peak corresponding to $HbA_{1c}$ and the peaks corresponding to $HbA_0$, $HbA_{1b}$ or $HbA_{1a}$), are superimposed or overlap, then the test compound is not considered to be appropriate for carrying out the invention.

The concentration of the test compound in the test indicated above is given solely by way of indication; if a concentration of 10 to 120 mM of test compound cannot produce sufficient separation between the peak corresponding to $HbA_{1c}$ and the peak corresponding to the other haemoglobins of the sample in the context of the test indicated above, it is possible to go beyond this concentration range in order to obtain optimal separation of the peak corresponding to $HbA_{1c}$.

Any chemical compound (i.e. generally an organic molecule), any antibody, polypeptide, peptide, or any other compound which is capable of specifically complexing glucose residues and of providing negative charges at an alkaline pH in the sense of the present invention may be used in the context of the present invention. An appropriate antibody may be generated using any method which is known to the skilled person and may, for example, be a polyclonal or monoclonal antibody, a chimeric antibody or a fragment of antibody, for example a Fab fragment.

As can be seen in the "examples" section, boric acid is not a chemical compound which is capable of specifically complexing glucose residues and of providing negative charges at an alkaline pH in the sense of the present invention as it does not enable performing a reliable analysis and in particular a reliable assay of glycated haemoglobins and in particular of $HbA_{1c}$. Examples of appropriate chemical compounds are defined in more detail below.

Each glucose residue complexed with the compound which is capable of specifically complexing glucose residues interacts with a different molecule of compound.

According to a particular embodiment, when it is present in sufficient quantity in the buffer composition of the invention, said compound is in particular capable of specifically complexing the N-terminal glucose residue(s) of a glycated haemoglobin, i.e. for each globin chain (in particular beta) comprising a glucose residue bond to the amino acid in the N-terminal position, of specifically complexing said glucose residue. Said compound is thus capable of specifically complexing each glucose residue which is bound in the N-terminal position on the beta chains of a $A_{1c}$ haemoglobin or of a $S_{1c}$ or $C_{1c}$ haemoglobin.

According to a particular embodiment, when it is present in sufficient quantity in the buffer composition of the invention, said compound is capable of specifically complexing all the glucose residues of the haemoglobins glycated in the N-terminal position by a glucose.

According to a particular embodiment, when it is present in sufficient quantity in the buffer composition of the invention, said compound is capable of specifically complexing all of the glucose residues of a haemoglobin, regardless of their position on the globin chain(s). Thus, when said compound is present in sufficient quantity in the buffer composition of the invention, a haemoglobin molecule comprising a number x of glucose residues can bind a number x of molecules of said compound.

By specifically complexing with one or several glucose residue(s) of glycated haemoglobin(s) of a biological sample, said compound provides said glycated haemoglobin or haemoglobins with several negative electrical charges at an alkaline pH, i.e. enables surcharging these glycated haemoglobin(s) with negative electric charges at an alkaline pH.

Said compound provides each glucose residue of the same haemoglobin complexed thereby with several negative electric charges at an alkaline pH. Because of this provision of negative electric charges at an alkaline pH, the electrophoretic mobility of the haemoglobins comprising at least one glucose residue is modified as a result of their complexing with said compound. This is manifested on an electrophoretic profile by the displacement of the electrophoresis peak(s) corresponding to the glycated haemoglobins comprising one or several glucose residue(s) which are present in the analyzed biological sample.

All of the haemoglobins comprising at least one glucose residue which are present in the biological sample form a complex with the compound complexing glucose and providing negative electric charges at an alkaline pH (of course providing that said compound is present in sufficient quantity to complex with each of these haemoglobins). However, the different haemoglobins and in particular the different haemoglobins comprising at least one glucose residue all have a different isoelectric point (due to the nature of their globin chains, the number and the position of the glucose residue(s) on those globins chains and the number, nature and position of other sugars that may be bound to said haemoglobins). Because of the negative electric charges at an alkaline pH provided by the complexing of each glucose residue with said compound, the difference in charge between these various haemoglobins is even more marked when they are in the form which is complexed with said compound.

The glycated haemoglobins which include a glucose residue bound to the amino acid in the N-terminal position on at least one of their globin chains (in particular on the beta chains) thus have at least one glucose more than the other haemoglobins (differently glycated or non-glycated). In particular, haemoglobin $A_{1c}$ has at least one more glucose on the beta chains than the other minor fractions of haemoglobin $A_1$. As a consequence, when they are complexed according to the invention, these haemoglobins glycated in the N-terminal position are more heavily loaded with negative electric charges at an alkaline pH by said compound than the other haemoglobins (the glycated haemoglobins not comprising a glucose residue bound to the N-terminal amino acid of the globin chains or the non-glycated haemoglobins).

Thus, by increasing the difference in electrophoretic mobility existing between the various haemoglobins comprising glucose and/or between one or several haemoglobin(s) comprising glucose and the other haemoglobins present in the analyzed biological sample, better separation is achieved between one or several haemoglobin(s) glycated in the N-terminal position and the other haemoglobin(s) which may be present in said sample, in particular between haemoglobin $A_{1c}$ and the other minor fractions of haemoglobin $A_1$ haemoglobin which may be present in said sample.

Thus, the method of the invention can effectively separate haemoglobins glycated in the N-terminal position, in particular $HbA_{1c}$, from other haemoglobins, from certain variants and from other minor fractions present in a biological sample containing other haemoglobins. Furthermore, conventional interfering molecules such as labile, acetylated or carbamylated forms do not interfere with the assay of $HbA_{1c}$ using the method of the invention. In particular, the method of the invention enables to avoid interferences which may result, in the absence of negative electric charges at an alkaline pH provided by complexing, from the co-migration of haemoglobin $A_{1c}$ and by other minor fractions of haemoglobin $A_1$ (including $HbA_{1a}$ and $HbA_{1b}$) present in the biological sample, during the electrophoretic separation step.

The separated haemoglobin(s) glycated in the N-terminal position may then be assayed in the presence of other or of the other haemoglobins which may be present in the analyzed biological sample. Thus, as an example, $HbA_{1c}$ may be assayed in the presence of other minor fractions of haemoglobin $A_1$ and in particular in the presence of $HbA_{1a}$ and/or $HbA_{1b}$ without these other minor fractions present in the analyzed biological sample interfering with that assay.

The term "to assay" or "assay" in the present application means that the quantity of haemoglobin or haemoglobins of interest, possibly in the presence of one or several other haemoglobin(s) of the analyzed biological sample, is determined and/or the proportion of said haemoglobin(s) of interest is determined with respect to the total quantity of haemoglobin or with respect to the quantity of certain haemoglobins present in said sample.

The assay carried out in the context of the invention may be semi-quantitative; thus, the percentage of a given haemoglobin is measured with respect to the quantity of another haemoglobin or the other haemoglobin(s) present in said sample.

Thus, in the case of $HbA_{1c}$, in general the percentage of $HbA_{1c}$ is measured with respect to the quantity of one or several other A haemoglobin(s); in general, the area of the electrophoretic peak corresponding to $HbA_{1c}$ is divided by the area of the peak corresponding to $HbA_0$ or by the sum (area of peak corresponding to $HbA_{1c}$+area of peak corresponding to $HbA_0$), by the sum (area of all of the HbA peaks) or by the sum (area of peak corresponding to $HbA_{1c}$+area of peak corresponding to $HbA_0$+area of peak corresponding to $HbA_2$), or even by the total surface area of the electrophoretic profile.

The assay may also be quantitative; the results are then expressed in millimoles (mmoles) of a given haemoglobin per mole of another haemoglobin or other haemoglobin(s) present in said sample, for example in mmoles of $HbA_{1c}$ per mole of HbA.

According to a particular embodiment of the invention, the compound specifically complexing glucose residue(s) of glycated haemoglobin(s) and providing said glycated haemoglobins with negative charges at an alkaline pH comprises several functional groups, in particular two or more than two functional groups.

At least one of said functional groups specifically complexes a glucose residue (in particular a glucose residue bond to the amino acid in the N-terminal position on a globin chain) by interacting, for example, with a cis-diol group, in particular with two vicinal hydroxyl groups, of a glucose residue. As an example, this(these) group(s) may be a boronate group, in particular a boronate group as defined in the present application.

Said glucose complexing group(s) may provide glycated haemoglobin with one negative electric charge at an alkaline pH per complexed glucose residue, i.e. one or several negative charge(s) at an alkaline pH per complexed haemoglobin molecule (one negative charge if the haemoglobin molecule comprises only one glucose residue and n negative charges if the haemoglobin molecule comprises n glucose residues).

The other, one of the others, or the other functional group(s) of said compound (i.e. the functional group(s) which do not complex with glucose) provide(s) glycated haemoglobin with one or several negative electric charge(s) at an alkaline pH for each complexed residue of glucose of a molecule of said haemoglobin.

Thus, in this particular embodiment of the invention, each molecule of compound specifically complexing glucose residues according to the invention comprises at least one functional group which is capable of complexing a glucose residue of a glycated haemoglobin (and in particular a N-terminal glucose residue of a haemoglobin glycated in the N-terminal position) and at least one functional group which does not complex glucose but enables surcharging said glycated haemoglobin with negative charges at an alkaline pH since it provides said glycated haemoglobin with one or several supplemental negative charge(s) at an alkaline pH. The functional group which is capable of complexing glucose may also provide a negative electric charge at an alkaline pH.

According to a particular embodiment of the invention, the compound specifically complexing glucose residues and providing negative charges at an alkaline pH (more precisely each molecule of said compound) provides a glycated haemoglobin molecule, and in particular to a haemoglobin glycated in the N-terminal position, with several negative electric charges at an alkaline pH, for each complexed residue of glucose of said glycated haemoglobin molecule. Preferably, for each complexed glucose residue, it provides one glycated haemoglobin molecule with at least two (in particular two, three, four, five or six) negative electric charges at an alkaline pH.

According to a particular embodiment of the invention, the functional group or at least one of the functional groups specifically complexing glucose residues is negatively charged at an alkaline pH.

According to a particular embodiment of the invention, the compound which is capable of specifically complexing glucose residues of glycated haemoglobins and of providing said glycated haemoglobins with negative charges at an alkaline pH comprises one or several groups which are ionisable (in particular anionisables) at an alkaline pH. Said compound may be of various types. For example, the compound may comprise one or several carboxylate(s), carboxyl(s), sulphonate(s) and/or sulphonyl(s). Said compound may in particular be a polycarboxylic acid, in particular a dicarboxylic or tricarboxylic acid. Said compound may also be a polysulphonic acid, in particular a disulphonic or trisulphonic acid.

According to a particular embodiment of the invention, the group, one of the groups or the groups providing a glycated haemoglobin molecule with one or several negative electric charge(s) at an alkaline pH for each complexed glucose residue of said glycated haemoglobin molecule comprises or consists of one or several group(s) which are ionisable at an alkaline pH as defined in the present application, and in particular one or several (in particular two or three) carboxylate, carboxyl, sulphonate and/or sulphonyl group(s).

According to a particular embodiment of the invention, the group, one of the groups or the groups specifically complexing glucose residues comprise or consist of one or several boronate group(s).

In the present application, the term "boronate group", means a group with formula:

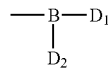

in which $D_1$ and $D_2$ are selected, independently of each other, from a hydroxyl group and a group susceptible of being hydrolyzed to produce a hydroxyl group in aqueous solution, in particular at an alkaline pH.

In a particular embodiment of the invention, said boronate group is the group —$B(OH)_2$, (also known as a boronyl group) or an ionized form, in particular —$B(OH)^-_3$.

In a particular embodiment of the invention, the compound which is capable of specifically complexing glucose residues of glycated haemoglobins and providing said glycated haemoglobins with negative charges at an alkaline pH is:

(i) a boronate compound, with general formula $RB(OH)_2$ (compound also known as boronic acid), or with general formula $RB(OH)^-_3$, wherein the group R comprises at least one aryl and/or an alkyl (linear, branched or cyclic) and/or an aralkyl and/or a combination thereof, and said group R provides glycated haemoglobins with one or several negative electric charge(s) at an alkaline pH for each glucose residue complexed with the boronate group; or (ii) a salt of said boronate compound.

Thus, at an alkaline pH, in addition to the negative electric charge at an alkaline pH provided by the boronyl or boronate of the boronate compound or its salt, the group R provides glycated haemoglobins with one or several supplemental negative electric charge(s) for each glucose residue complexed with the boronyl or boronate group.

In the context of the present application, the term "compound with general formula $RB(OH)_2$" also means any ionic form in equilibrium therewith, in particular $RB(OH)^-_3$, or any form that is capable of being in equilibrium therewith depending on the conditions of the medium.

In the context of the present application, the term "salt" denotes any salt and in particular a sodium, lithium or potassium salt.

The group R of the boronate compound of the invention may also include other functions and/or heteroatoms, in addition to the aryl, alkyl, aralkyl function(s) or one of their combinations.

According to a particular embodiment, for each glucose residue complexed with the boronyl or boronate group of the boronate compound of the invention or its salt, the group R provides two or more (preferably two) negative electric charges at an alkaline pH.

According to a particular embodiment, the group R consists of one or several aryl(s), alkyl(s) (linear, branched or cyclic) and/or aralkyl(s) and/or a combination thereof.

According to a particular embodiment, the aryl(s), alkyl(s), aralkyl(s) or other functional groups and/or heteroatoms or their combinations present in the group R of the boronate compound of the invention may be substituted.

The term "substituted" as used in the present application may signify mono-substituted or, in contrast, polysubstituted, in particular di-, tri-, tetra-, penta- or hexa-substituted.

The substituents may in particular be groups which are ionizable (in particular anionisables) at an alkaline pH as defined in the present application. The group R may include one or several heteroatoms, or other functional groups.

According to a particular embodiment of the invention, the group R of the boronate compound provides a glycated haemoglobin molecule with one or several negative electric charges at an alkaline pH for each complexed glucose residue. Preferably, for each complexed glucose residue, it provides a glycated haemoglobin molecule with one, two, three or four negative electric charges at an alkaline pH.

A boronate compound as defined above in particular comprises boronic acids, and in particular phenylboronic acids.

According to a particular embodiment of the invention, the compound which is capable of specifically complexing glucose residues of glycated haemoglobins and of providing said glycated haemoglobins with negative charges at an alkaline pH is a polysubstituted phenylboronate, in particular a disubstituted phenylboronate, for example disubstituted with carboxyl and/or sulphonyl groups.

According to a particular embodiment of the invention, the group R of the boronate compound or its salt is a diacid, in particular a dicarboxylic acid. According to a particular embodiment of the invention, the boronate compound is a dicarboxyphenylboronic acid, preferably selected from 3,5-dicarboxyphenylboronic acid and 3,4-dicarboxyphenylboronic acid.

Thus, by way of example, the boronate compound employed may be 3,5-dicarboxyphenylboronic acid (3,5-dCPBA). This compound is commercially available, in particular from the supplier Combi-blocks Inc. (San Diego, USA), under the trade name 3,5-dicarboxyphenylboronic acid and from Apollo Scientific Ltd (Cheshire, United Kingdom), under the trade name 3,5-dicarboxybenzeneboronic acid.

In the buffer composition of the invention, the concentration of the compound which is capable of specifically complexing glucose residues of glycated haemoglobins and of providing said glycated haemoglobins with negative charges at an alkaline pH is generally in stoichiometric excess with respect to the total quantity of proteins, in particular with respect to the total quantity of all of the haemoglobins present in the biological sample or with respect to the total quantity of all of the haemoglobins comprising glucose present in the biological sample. Thus, the quantity of this compound in the buffer composition is greater than the quantity necessary for all of the glucose residues of the haemoglobins present in the sample to be complexed by said compound when the sample or an aliquot of that sample is diluted in the buffer composition. Thus, for each molecule of glycated haemoglobin comprising glucose present in the analyzed biological sample, there are at least as many molecules of that compound in the buffer composition as there are glucose residues present in this glycated haemoglobin molecule. This enables achieving a complete separation of the glycated haemoglobin or glycated haemoglobins of interest from the other haemoglobins also present in the analyzed biological sample.

According to a particular embodiment of the invention, in the buffer composition of the invention, the concentration of compound which is capable of specifically complexing glucose residues of glycated haemoglobins and of providing said glycated haemoglobins with negative charges at an alkaline pH is in the range 0.10 to 100 mM, preferably in the range 10 to 60 mM, and more preferably in the range 20 to 50 mM, for example 30 mM or 50 mM.

The expression "in the range x to y" as used in the present application means that the limits x and y are included in the indicated range x-y.

According to a particular embodiment, the buffer composition of the invention further comprises:
 a buffer compound with a pKa in the range 8.0 to 11.0; and/or
 a flow retardant; and/or
 a base; and/or
 a salt; and/or
 an appropriate dilution solution, for example water.

Thus, the buffer composition of the invention comprises or consists of (i) a compound which is capable of specifically complexing glucose residues of glycated haemoglobins and of providing said glycated haemoglobins with negative charges at an alkaline pH, and (ii) one or several and in particular all of the compounds selected from: a buffer compound having a pKa in the range 8.0 to 11.0, a flow retardant, a base, a salt, an appropriate diluting solution (for example water) and mixtures thereof.

The buffer compound is preferably a zwitterionic compound. It may in particular be selected from AMP, AMPD, AMPSO, bicine, CABS, CAPS, CAPSO, CHES, HEPBS, methylamine, TABS, TAPS, taurine, tricine and Tris; in particular, CAPS, CAPSO or CHES are selected, preferably CHES. These compounds have a high buffering power at the target pH (pH 8-11) and are particularly suitable for obtaining good focussing of the haemoglobins.

The concentration of buffer compound in the buffer composition of the invention is generally in the range 20 to 500 mM, preferably in the range 50 to 400 mM, and more preferably in the range 100 to 350 mM or in the range 150 to 300 mM, for example approximately 200 mM or approximately 300 mM.

The flow retardant is intended to strengthen the effect of the differences in electric charge in order to obtain a good resolution of separation between the various haemoglobins. This type of compound acts by reducing the electro-osmotic flux, which retards migration of the various fractions and can increase their separation. The flow retardant used may be an aliphatic diamine, in particular an aliphatic diamine selected from 1,3-diaminopropane, 1,4-diaminobutane (putrescine), 1,5-diaminopentane (cadaverine), 1-6-diaminohexane, spermine and DETA, or a derivative of said aliphatic diamine or a mixture thereof.

The term "derivative" as used herein means an aliphatic polyamine, a cyclic polyamine, a salt (for example a sodium salt) or one of their mixtures.

According to a particular embodiment of the invention, the flow retardant is selected from putrescine, its derivatives and mixtures thereof.

According to a particular embodiment of the invention, the flow retardant is putrescine. In particular, putrescine is in the pure form, a salt being optionally added.

According to another particular embodiment of the invention, the flow retardant is putrescine hydrochloride (or putrescine-2HCl).

In the buffer composition of the invention, the concentration of flow retardant is advantageously in the range 0.10 to 40 mM, preferably in the range 10 to 30 mM and more preferably in the range 15 to 25 mM, for example 20 mM.

The base optionally added to the buffer composition allows the pH of said composition to be adjusted. In particular, a base belonging to the hydroxide family may be used, in particular a base selected from lithium hydroxide, sodium hydroxide, potassium hydroxide, rubidium hydroxide, caesium hydroxide, francium hydroxide, a mono-, di-, tri- or tetra-alkyl ammonium hydroxide, and mixtures thereof.

According to a particular embodiment of the invention, the base optionally added to the buffer composition is sodium hydroxide.

Advantageously, sufficient base is added to the buffer composition so that its pH is 9.0 or more, preferably in the range 9.0 to 11.0 and more preferably in the range 9.0 to 10.0, for example in the range 9.3 to 9.5, and still more preferably a pH of 9.4 or 9.5. An alkaline pH of more than 9 can produce negatively charged haemoglobin fractions (the isoelectric point of haemoglobins being in the range 6.05 to 7.63).

According to a particular embodiment of the invention, the salt which is optionally present in the buffer composition of the invention is a sodium salt, preferably sodium chloride. The buffer composition may comprise for example 2.5 g/l of sodium chloride.

According to a particular embodiment of the invention, when the buffer composition comprises putrescine, in particular pure putrescine, it further comprises a salt (in particular a sodium salt), preferably sodium chloride, for example 2.5 g/l of sodium chloride.

According to another particular embodiment of the invention, the buffer composition comprises putrescine hydrochloride, does not comprise sodium chloride and preferably does not comprise any salt.

According to a particular embodiment of the invention, the buffer composition comprises or consists of:
 200 mM of CAPSO;
 10 mM of putrescine (for example either putrescine-2HCl or pure putrescine and sodium chloride);
 50 mM of 3,5-dicarboxyphenylboronic acid;
 water; and
 if necessary, a base, for example sodium hydroxide, to adjust the pH, for example to a value greater than 9 or 10, and preferably to a value of 10.2;
or, more preferably, of:
 200 mM of CAPSO;
 15 mM of putrescine (for example either putrescine-2HCl or pure putrescine and sodium chloride);
 100 mM of 3,5-dicarboxyphenylboronic acid;
 water; and
 if necessary, a base, for example sodium hydroxide, to adjust the pH, for example to a value greater than 9 or 10, and preferably to a value of 10.2;

or, still more preferably, of:
  200 mM of CHES;
  20 mM of putrescine (for example either putrescine-2HCl or pure putrescine and sodium chloride);
  30 mM of 3,5-dicarboxyphenylboronic acid;
  water; and
  if necessary, a base, for example sodium hydroxide, to adjust the pH, for example to a value greater than 9, and preferably to a value of 9.4.

According to another particular embodiment of the invention, the buffer composition comprises or consists of the components indicated above in the concentrations indicated above, and one or several salt(s), in particular a sodium salt, especially sodium chloride, for example 2.5 g/l of sodium chloride.

As illustrated in the example section, such buffer compositions enable achieving a perfect separation of haemoglobin $HbA_{1c}$ from the other haemoglobins present in the biological sample analyzed, as well as mutual separation of the various minor fractions (including $HbA_{1a}$, $HbA_{1b}$ and $HbA_{1c}$) in a manner unequalled in the field of free solution capillary electrophoresis.

The term "biological sample" as used in the present application means any biological fluid comprising red blood cells. Said biological fluid may derive from a healthy or sick human patient (for example a diabetic patient) or be of animal origin, in particular deriving from a non-human mammal (healthy or sick). Said biological liquid (human or non-human mammal) may, for example, be blood, in particular normal or non-normal blood, washed, decanted, centrifuged, haemolysed or whole blood. The biological samples may also be of synthetic or purified origin.

The invention is of particular application in the analysis of blood samples, in particular for the analysis of a blood sample deriving from a diabetic patient or from a diabetic non-human mammal.

According to a particular embodiment, said biological sample comprises or consists of several haemoglobins, in particular several glycated haemoglobins comprising a glucose residue bound to the amino acid in the N-terminal position on at least one globin chain (for example on the beta chains), and more particularly haemoglobin $A_{1c}$.

The biological sample used may be diluted prior to analysis by capillary electrophoresis with a suitable diluting solution, for example a haemolyzing solution and/or an analyzing buffer solution, in particular the buffer composition of the invention. Preferably, the analysis is carried out using a sample of haemolyzed blood.

According to another particular embodiment, the biological sample is initially diluted in a haemolyzing solution, then in the buffer composition of the invention.

The term "haemolyzing solution" as used in the present application designates a solution capable of causing haemolysis of red blood cells, i.e. the destruction of red blood cells, and thus of liberating haemoglobin. Depending on its composition, it can carry out total lysis of the red blood cells, optionally by employing a small additional mechanical action (vortex, stirring, etc). The haemolyzing solution may include the usual additives for cell lysis, such as Triton X100, which is usually used in a concentration of 1 g/L. The haemolyzing solution may also optionally include a compound which is capable of specifically complexing glucose residues of glycated haemoglobins and of providing said glycated haemoglobins with negative charges at an alkaline pH as defined in the present application.

By way of example, the haemolyzing solution may be selected from the group constituted by the haemolyzing solution Capillaries® Hemoglobin(e) from Sebia, the haemolyzing solution MINICAP® Hemoglobin(e) from Sebia, the haemolyzing solution Hydragel® $HbA_{1c}$ from Sebia, pure water, water supplemented with surfactant, in particular water supplemented with Triton X100 (for example 1g/L of Triton X100), and mixtures thereof.

According to a particular embodiment, the method for analysis by capillary electrophoresis of the invention comprises the following steps:
  a) introducing the buffer composition of the invention and the biological sample into an electrophoresis capillary; and
  b) separating the constituents of said biological sample by capillary electrophoresis.

These two steps are generally preceded by a step for dilution of the biological sample, for example in a haemolyzing solution. This dilution step may in particular be carried out in the sample support, for example in a Capillaries® (Sebia) dilution segment or in the MINICAP® (Sebia) sample cup.

In step a), the buffer composition of the invention and the biological sample may be introduced separately (simultaneously or not) into the same electrophoresis capillary, the mixture then being produced in the capillary. As an example, it is possible to introduce the buffer composition of the invention first, then the sample into the electrophoresis capillary.

Alternatively, the biological sample may be introduced into an electrophoresis capillary in step a) in the form of a mixture with the buffer composition of the invention.

Depending on the type of capillary electrophoresis apparatus used and as a function of the number of analyses to be carried out, a single capillary or several capillaries in parallel are used. When a single capillary is used, this capillary is generally used several times in succession, in order to carry out several analyses. Of course, when several capillaries are used, if necessary several electrophoretic migrations can be carried out in succession, during which several capillaries are used in parallel.

The step for separating the constituents of the biological sample by capillary electrophoresis in particular consists of applying to the capillary(ies) an electric field with a sufficient voltage to allow the separation of one or several glycated haemoglobin(s) of interest from other proteins and in particular from other haemoglobins which may be present in the biological sample.

The conditions for carrying out liquid capillary electrophoresis are the conditions generally used by the skilled person for the steps of introducing the sample and the buffer composition into the capillary(ies) and separating the constituents of the sample by electrophoretic migration. The electric field applied may, for example, be approximately 400 V/cm. They usually comprise washing the capillaries with a washing solution, washing with the buffer composition used for the analysis, optionally diluting the sample one or more times, introducing the sample into the capillary(ies), migration and detection. These steps may be carried out by automated machines.

The conditions for carrying out capillary electrophoresis are, for example, conditions suitable for using the Capillaries® automated machine from Sebia or the MINICAP® from Sebia.

The step for separating the constituents of the biological sample is generally followed by a step for detection of one or several protein(s), in particular one or several haemoglobins present in the biological sample, and more particularly one or several glycated haemoglobins of interest present in the biological sample, for example haemoglobin $A_{1c}$.

This detection step may in particular be carried out by measuring the absorbance, for example at a wavelength of approximately 415 nm, which is specific to haemoglobin; the haemoglobins may be analyzed at a wavelength of approximately 200 nm, but in order to avoid interference with plasma proteins in particular, they are preferably analyzed at a wavelength of 415 nm.

In the context of the invention, the results of the electrophoretic separation may be presented as illustrated in the examples, in the form of electrophoretic profiles generated from a detection signal proportional to the quantity of haemoglobin detected. Thus, the method of the invention generally further comprises a step for generating an electropherogram from the detection signal.

As indicated above, when it is present in the analyzed biological sample, a haemoglobin of interest may be quantified. To this end, the surface area of the peak corresponding to said haemoglobin is determined.

Thus, said method generally also comprises a step for determining, in particular from an electropherogram, the quantity of one or several haemoglobin(s) present in the biological sample and/or the proportion of one or several haemoglobin(s) present in the biological sample with respect to the total quantity of proteins, to the total quantity of haemoglobin and/or to the quantity of certain haemoglobins (for example with respect to the quantity of HbA or $HbA_0$) present in the biological sample. In particular, the proportion of glycated haemoglobin $A_{1c}$, $S_{1c}$ and/or $C_{1c}$ present in the biological sample with respect to the total quantity of all of the haemoglobins or with respect to the quantity of certain haemoglobin(s) present in the biological sample, for example with respect to the total quantity of A, S and/or C haemoglobin respectively, can be determined.

In one particular embodiment of the invention, this assay may be obtained directly from the electrophoretic profile.

According to a particular embodiment of the invention, the analysis method also comprises a step for quantification of one or several haemoglobin(s) present in the analyzed biological sample with respect to one or several standardized calibrator(s) (for example one or several reference biological samples); this enables standardization of the results.

Thus, in order to obtain a high level of precision during assay, each capillary is generally calibrated every time the electrophoresis apparatus is started up, using reference biological samples (for example standard samples containing known concentrations of different natural and/or synthetic fractions of glycated haemoglobin, purified if necessary). As an example, in order to assay $HbA_{1c}$, at least two calibrators are generally used, for example a first calibrator comprising a known high concentration of $HbA_{1c}$ and a second calibrator comprising a low known concentration of $HbA_{1c}$. Then, with each capillary of the electrophoresis apparatus, the quantity of $HbA_{1c}$ present in each calibrator is measured. This enables to establish a regression curve (over at least two points) for each capillary, and thus the measurements carried out using the various capillaries can be normalized. This also enables standardization of the results obtained with respect to a reference method, by using values for $HbA_{1c}$ determined by this method for the calibrators.

According to a particular embodiment of the invention, the capillary electrophoresis carried out is a free solution capillary electrophoresis, in particular is a naked capillary(ies) free solution capillary electrophoresis.

From the point of view of the materials used for the capillaries, those that are normal for capillary electrophoresis are employed. The specialist will be able to adapt the nature of the capillary and its size to the requirements of the analysis.

As an example, in a particular embodiment, the electrophoresis capillary(ies) is (are) of fused silica.

The present invention also pertains to the use of the capillary electrophoresis analysis method according to the invention for separating one or several glycated haemoglobin(s) comprising glucose, more precisely one or several glycated haemoglobin(s) each comprising, on one or several globin chain(s) (for example on the beta chains), one or several glucose residue(s) bound to the amino acid in the N-terminal position, from other proteins, in particular from at least one other haemoglobin, and preferably from the other haemoglobins present in a biological sample and, if appropriate, to assay said glycated haemoglobin(s).

The present invention also pertains to a buffer composition suitable for capillary electrophoretic analysis of a biological sample comprising haemoglobins and in particular one or several glycated haemoglobin(s), more particularly one or several glycated haemoglobin(s) comprising one or several glucoses on one or several globin chains (for example on the beta chains). Said buffer composition comprises at least one compound that is capable of specifically complexing glucose residues of glycated haemoglobins and also of providing said haemoglobin(s) with several negative electric charges at an alkaline pH.

Said buffer composition is in particular that used to carry out the method for capillary electrophoresis of a biological sample presented in the present application.

In particular, according to a particular embodiment of the invention, the buffer composition comprises a polycarboxylic boronic acid, in particular a dicarboxylic acid or a tricarboxylic acid, for example 3,5-dicarboxyphenylboronic acid, as a compound which can specifically complex glucose residues and provide negative electric charges at an alkaline pH.

According to another particular embodiment of the invention, the buffer composition comprises, in addition to the compound which is capable of specifically complexing glucose residues and of providing negative electric charges at an alkaline pH, a flow retardant; and/or
a buffer compound with a pKa in the range 8.0 to 11.0; and/or
a base; and/or
a salt (in particular a sodium salt, for example sodium chloride); and/or
an appropriate diluting solution, for example water.

These various constituents may be as defined in the present application.

According to a particular embodiment of the invention, the buffer composition has a pH of 9.0 or more, preferably a pH in the range 9.0 to 11.0 and more preferably a pH in the range 9.0 to 10.0, for example a pH in the range 9.3 to 9.5, and still more preferably a pH of 9.4. Such a pH may in particular be obtained by providing a sufficient quantity of a base as defined above.

The buffer compositions of the invention are prepared in the usual manner for analytical buffer compositions, namely by providing the constituents in the liquid form or in the solid form to be diluted, to an acceptable support. Usually, the support is water, distilled or demineralized.

The present invention also concerns a kit comprising a buffer composition of the invention and, if appropriate, instructions for use, to carry out electrophoretic analysis. In other words, the kit of the invention may comprise or consist of a buffer composition of the invention and a packaging material and, if appropriate, instructions for use.

Thus, the kit of the invention in particular comprises a compound which is capable of specifically complexing glucose residues of glycated haemoglobin and of providing negative charges at an alkaline pH as defined in the present application. When, in addition to said compound, said kit comprises other compounds, in particular one or several compound(s) selected from: a buffer compound with a pKa in the range 8.0 to 11.0, a flow retardant, a base, a salt (in particular a sodium salt, for example sodium chloride), an appropriate diluting solution (for example water) and mixtures thereof, the various compounds of said kit may be packaged for extemporaneous mixing, or, in contrast, may be packaged together, in particular in the same composition, in the form of a mixture. Alternatively, certain compounds of said kit may be packaged separately while others may be packaged together, in particular in the form of a mixture.

According to a particular embodiment of the invention, the buffer composition of the invention is provided in one or several parts, to be reconstituted by the consumer before the analysis. Hence, problems with stability which might arise for example when all of the components or some components of said composition are packaged in the form of a mixture can be overcome.

The kit of the invention may also comprise one or several solution(s) for washing the capillaries and/or one or several dilution segment(s) and/or one or several solution(s) suitable for diluting the biological sample to be analyzed (for example a haemolyzing solution, in particular a haemolyzing solution as defined in the present application) and/or one or several reference biological sample(s) (for example natural and/or synthetic glycated fractions, purified if necessary) which enable(s) calibrating each capillary.

The present invention also pertains to the use of a buffer composition as defined in the present application and/or to a kit of the invention for the analysis, by capillary electrophoresis, of (one or several) glycated haemoglobins comprising one or several glucose residue(s), in particular the $A_{1c}$, $S_{1c}$ and $C_{1c}$ haemoglobins contained in a biological sample comprising one or several haemoglobin(s).

The present invention also pertains to the use of a buffer composition as defined in the present application and/or a kit of the invention and/or a compound which is capable of specifically complexing glucose residues (one or several) of glycated haemoglobins (one or several glycated haemoglobin(s)) and of providing this or these glycated haemoglobin(s) with several negative electric charges at an alkaline pH to separate, by capillary electrophoresis, one or several glycated haemoglobin(s) comprising a glucose residue bound to the amino acid in the N-terminal position on at least one globin chain (for example on the beta chains), and more particularly to separate, by capillary electrophoresis, haemoglobin $A_{1c}$ from other proteins, in particular from at least one other haemoglobin and preferably from the other haemoglobins present in a biological sample and, if appropriate, to assay said haemoglobin(s) separated thereby.

In particular, the buffer composition of the invention, the kit of the invention and/or a compound which is capable of specifically complexing glucose residues of glycated haemoglobins and of providing negative electric charges at an alkaline pH as defined in the present application are appropriate for use, for example in the context of a method of the invention for diagnosing diabetes in a human or non-human mammal and/or for monitoring the glycaemic balance of a human or non-human mammal (in particular a diabetic subject), in particular to evaluate the efficacy of a treatment against diabetes and/or to adapt a diabetes treatment in a diabetic subject. The biological sample(s) analyzed then originate from said human or non-human mammal.

The term "diabetes" as used in the present application designates type 1 and/or type 2 diabetes.

The present invention also concerns the use of a buffer composition of the invention, of a kit of the invention and/or of a compound which is capable of specifically complexing glucose residues of glycated haemoglobins and of providing negative charges at an alkaline pH as defined in the present application, for the manufacture of a diagnostic kit. Said diagnostic kit may in particular be used for the diagnosis of diabetes in a human or a non-human mammal and/or to monitor the glycaemic balance of a human or non-human mammal, in particular a diabetic subject. Said kit may thus allow the efficacy of a treatment against diabetes in a human or a non-human mammal suffering from diabetes to be evaluated and/or allow a treatment against diabetes in a diabetic subject to be adapted.

The $HbA_{1c}$ level is generally in the range 4% to 6% (i.e. 20 to 42 mmoles of $HbA_{1c}$ per mole of haemoglobin in the blood) in a human non-diabetic, and more than 7% in a diabetic patient (in the absence of treatment).

In the case of $HbA_{1c}$ levels in the range 6% to 7% (i.e. a concentration of 42 to 53 mmoles of $HbA_{1c}$ per mole of haemoglobin in the blood), it is recommended that an anti-diabetic treatment be commenced.

Beyond a threshold of 8%, which is equivalent to a concentration of 64 mmoles of $HbA_{1c}$ per mole of haemoglobin in the blood (Panteghini and John, 2007), the patient runs an increased risk of developing one of the complications of diabetes (microangiopathy, macroangiopathy, etc). It is then recommended that the patient's anti-diabetic treatment be modified.

Other characteristics and advantages of the invention will become apparent from the following examples and figures which illustrate the invention.

EXAMPLES

A. Apparatus and Methods

Capillary Electrophoresis

The principle of separation is free solution capillary electrophoresis at an alkaline pH (pH>9), in order to obtain negatively charged haemoglobin fractions (the isoelectric point of haemoglobins is in the range 6.05 to 7.63).

The capillary electrophoresis of biological samples was carried out on a capillary electrophoresis apparatus provided with 8 fused silica capillaries with an internal diameter of 25 microns, a useful length of 16 cm and a total length of 18 cm (Capillaries® (Sebia) capillary electrophoresis system) or on capillary electrophoresis apparatus provided with one fused silica capillary with an internal diameter of 25 microns, with a useful length of 24 cm and a total length of 32 cm ($^{3D}$CE capillary electrophoresis system from Agilent Technologies).

Detection was carried out at a wavelength of 425 nm. The blood samples were diluted in a haemolyzing solution (Triton X100 1 g/L in water) and injected by hydrodynamic injection.

The capillary was washed before each analysis with 0.25 M sodium hydroxide, then with the buffer composition.

Buffer Composition

The buffer compositions in which the capillary electrophoresis was carried out comprised water, a buffer compound with a pKa in the range 8 to 11 (CAPS, CAPSO or CHES depending on the case), a base allowing the pH to be adjusted to the desired value, an optional flow retardant (putrescine), and an optional borate compound (boric acid) or boronate.

3,5-dicarboxyphenylboronic acid (3,5-dCPBA) was obtained from the firms Combi-blocks Inc. (San Diego, USA) and Apollo Scientific Ltd (Cheshire, United Kingdom).

3,4-dicarboxyphenylboronic acid (3,4-dCPBA) was synthesized by the firm BoroChem SAS (Caen, France).

B. Results

Example 1

Figure 1:
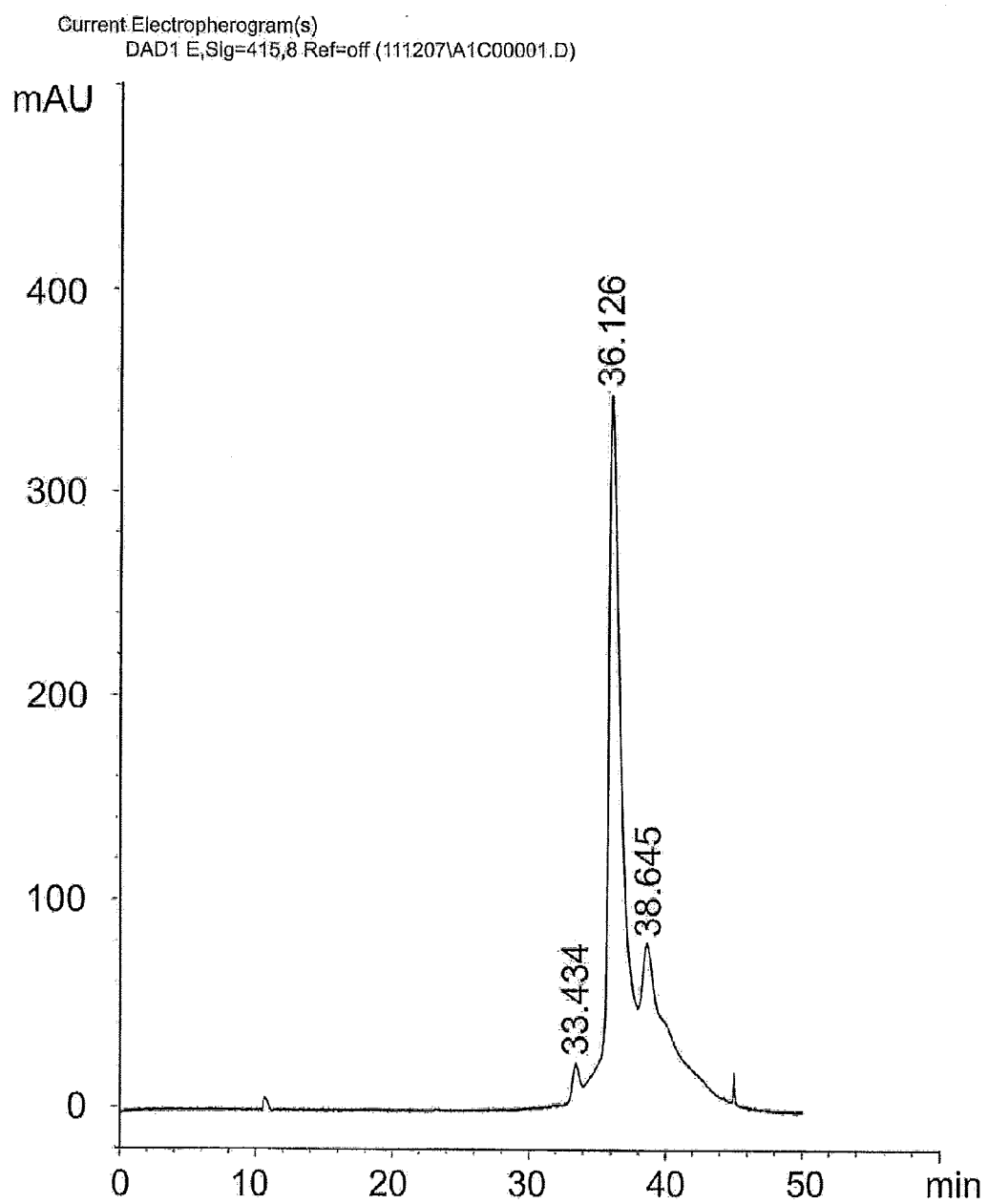
FIG. 1: electropherogram obtained on CE Agilent from a normal human blood sample using the analysis buffer described in patent U.S. Pat. No. 5,599,433, which contains 100 mM of CAPS and 300 mM of boric acid (pH: 11.00; temperature: 24° C.; voltage: 6.1 kV, i.e. 190 V/cm; injection: 50 mbars 20 s).

Capillary electrophoresis was carried out from normal human blood (comprising haemoglobins $HbA_0$, $HbA_1$ and $HbA_2$) diluted to ⅙th in a haemolyzing solution (1 g/L de Triton X100 dissolved in demineralized water), using the analysis buffer described in patent U.S. Pat. No. 5,599,433, which contained 100 mM of CAPS and 300 mM of boric acid, pH 11. The electropherogram obtained is presented in FIG. 1. The separation between the peaks of haemoglobins is poor.

Example 2

Figure 2:
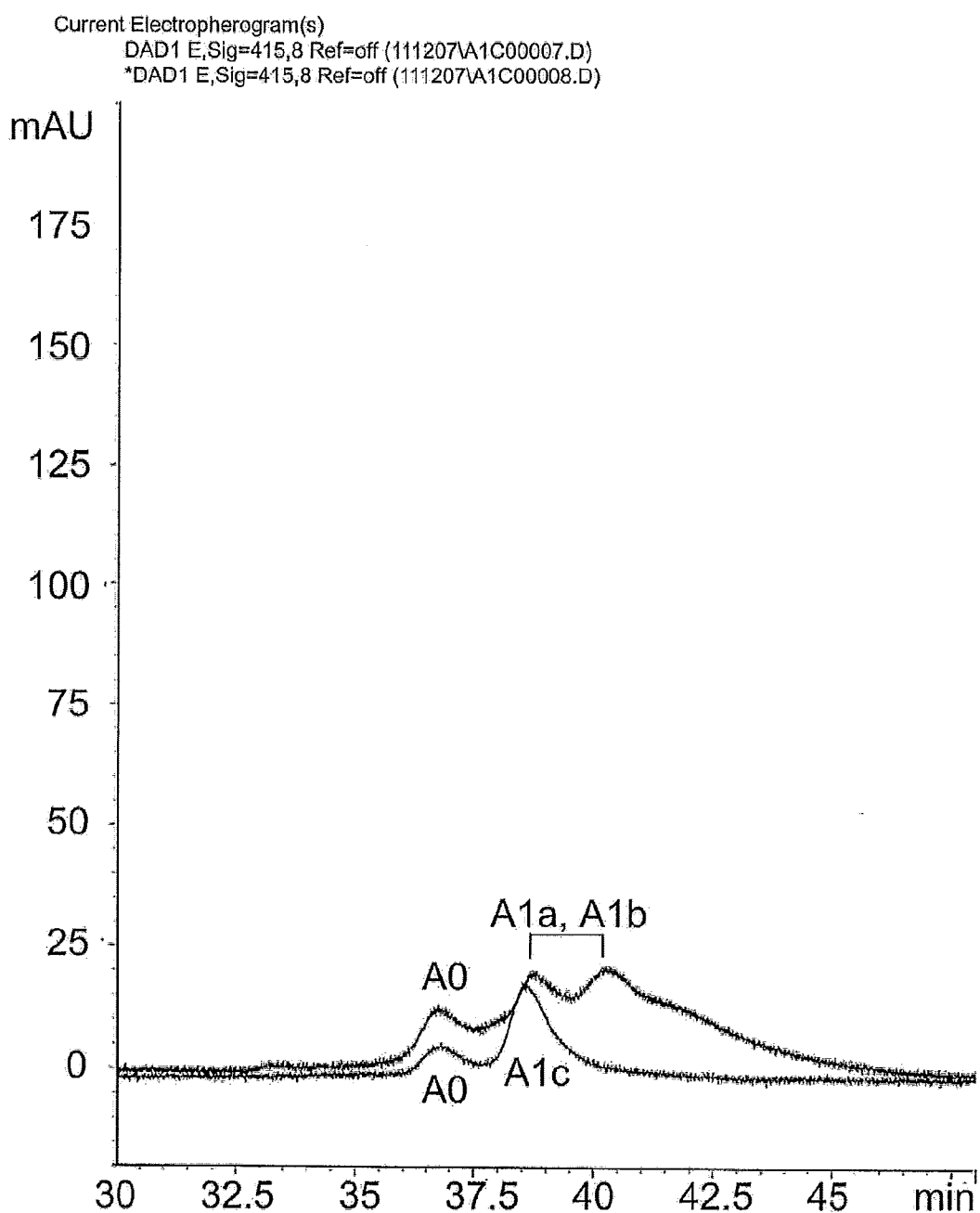
FIG. 2: standard electrophoretic profiles for $A_{1a,b}$ and $A_{1c}$ obtained on CE Agilent from reference samples containing different purified fractions of glycated haemoglobin using the analysis buffer described in patent U.S. Pat. No. 5,599,433, which contains 100 mM of CAPS and 300 mM of boric acid (pH: 11; temperature: 24° C.; voltage: 6.1 kV, i.e. 190 V/cm; injection: 50 mbars 20 s).

Capillary electrophoresis was carried out from reference samples (Exocell, USA), containing different purified fractions of glycated haemoglobin (fractions $A_0$ and $A_{1c}$ or fractions $A_0$, $A_{1b}$ and $A_{1a}$), using the analysis buffer described in patent U.S. Pat. No. 5,599,433, which contained 100 mM of CAPS and 300 mM of boric acid, pH 10.20. The standard electrophoretic profiles for $A_{1a,b}$ and $A_{1c}$ obtained are presented in FIG. 2. The separation between the $HbA_{1c}$ and $HbA_{1a,b}$ haemoglobins is clearly insufficient; the $HbA_{1c}$ electrophoretic peak overla
the $HbA1_a$/$HbA1_b$ peaks.

Example 3

Figure 3:
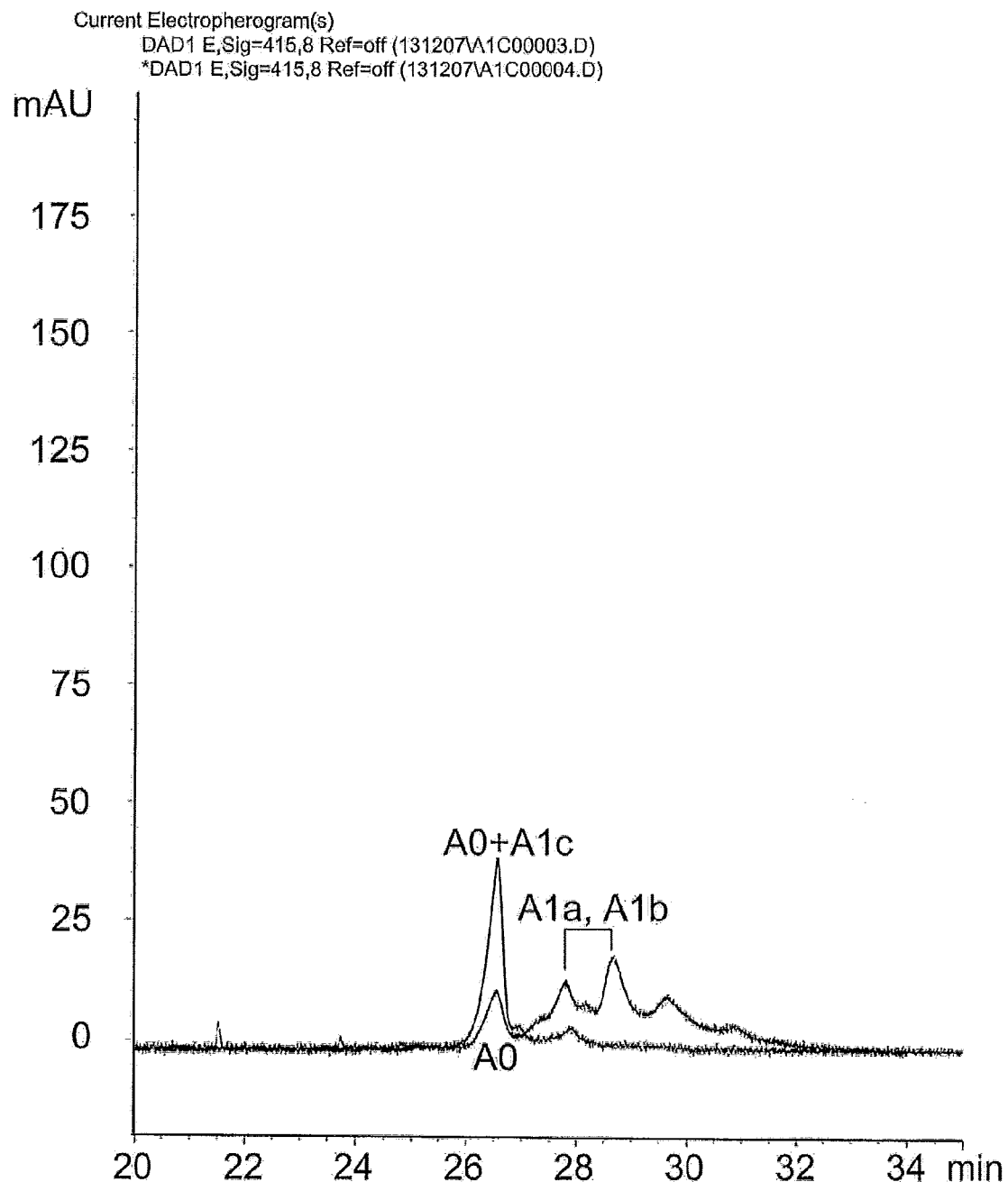
FIG. 3: standard electrophoretic profiles for $A_{1a,b}$ and $A_{1c}$ obtained on CE Agilent from reference samples containing different purified fractions of glycated haemoglobin, using a buffer composition containing 200 mM of CAPSO and 10 mM of putrescine but no borate compound, nor boronate compound (pH: 10.20; temperature: 24° C.; voltage: 6.1 kV, i.e. 190 V/cm; injection: 50 mbars 20 s).

Capillary electrophoresis was carried out from reference samples (Exocell, USA), containing different purified fractions of glycated haemoglobin (fractions $A_0$ and $A_{1c}$ or fractions $A_0$, $A_{1b}$ and $A_{1a}$), using a buffer composition containing 200 mM of CAPSO and 10 mM of putrescine (pH10.20) but no borate compound, and also no boronate compound. The standard electrophoretic profiles for $A_{1a,b}$ and $A_{1c}$ obtained are presented in FIG. 3. The peak corresponding to $HbA_{1c}$ co-migrated with that of $HbA_o$.

Example 4

Figure 4:
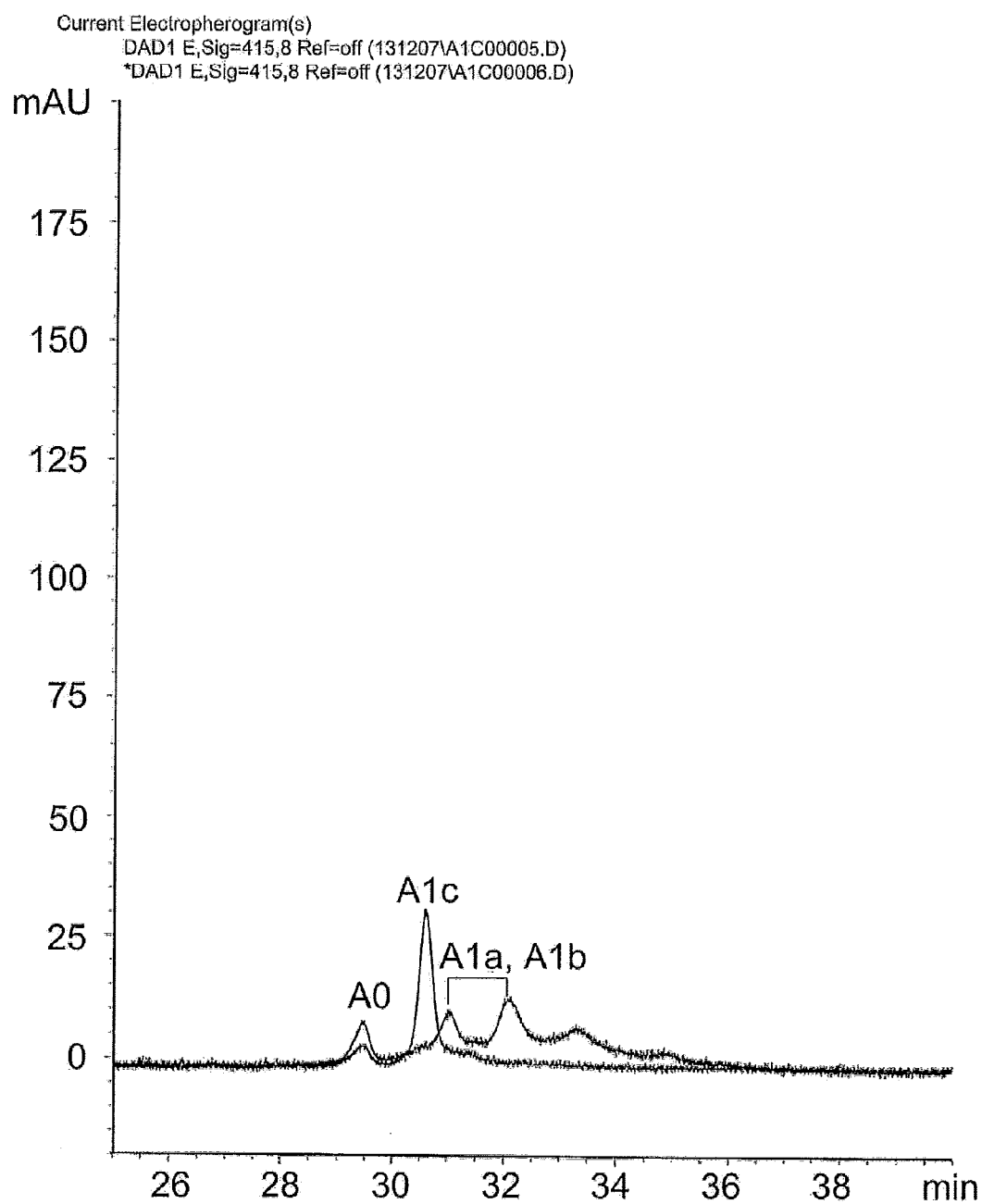
FIG. 4: standard electrophoretic profiles for $A_{1a,b}$ and $A_{1c}$ obtained on CE Agilent from reference samples containing different purified fractions of glycated haemoglobin, using a buffer composition containing 200 mM of CAPSO, 10 mM of putrescine and 50 mM de borate (pH: 10.20; temperature: 24° C.; voltage: 6.1 kV, i.e. 190 V/cm; injection: 50 mbars 20 s).

Capillary electrophoresis was carried out from reference samples (Exocell, USA), containing different purified fractions of glycated haemoglobin (fractions $A_0$ and $A_{1c}$ or fractions $A_0$, $A_{1b}$ and $A_{1a}$), using a buffer composition containing 200 mM of CAPSO, 10 mM of putrescine and 50 mM de borate (pH 10.20). The standard electrophoretic profiles for $A_{1a,b}$ and $A_{1c}$ obtained are presented in FIG. 4. The peak corresponding to $HbA_{1c}$ lies between the peaks corresponding to $HbA_o$ and $HbA_{1a}$/$HbA_{1b}$ and is too close to the peak corresponding to other $HbA_1$s to allow a reliable assay of $HbA_{1c}$.

Example 5

Figure 5:
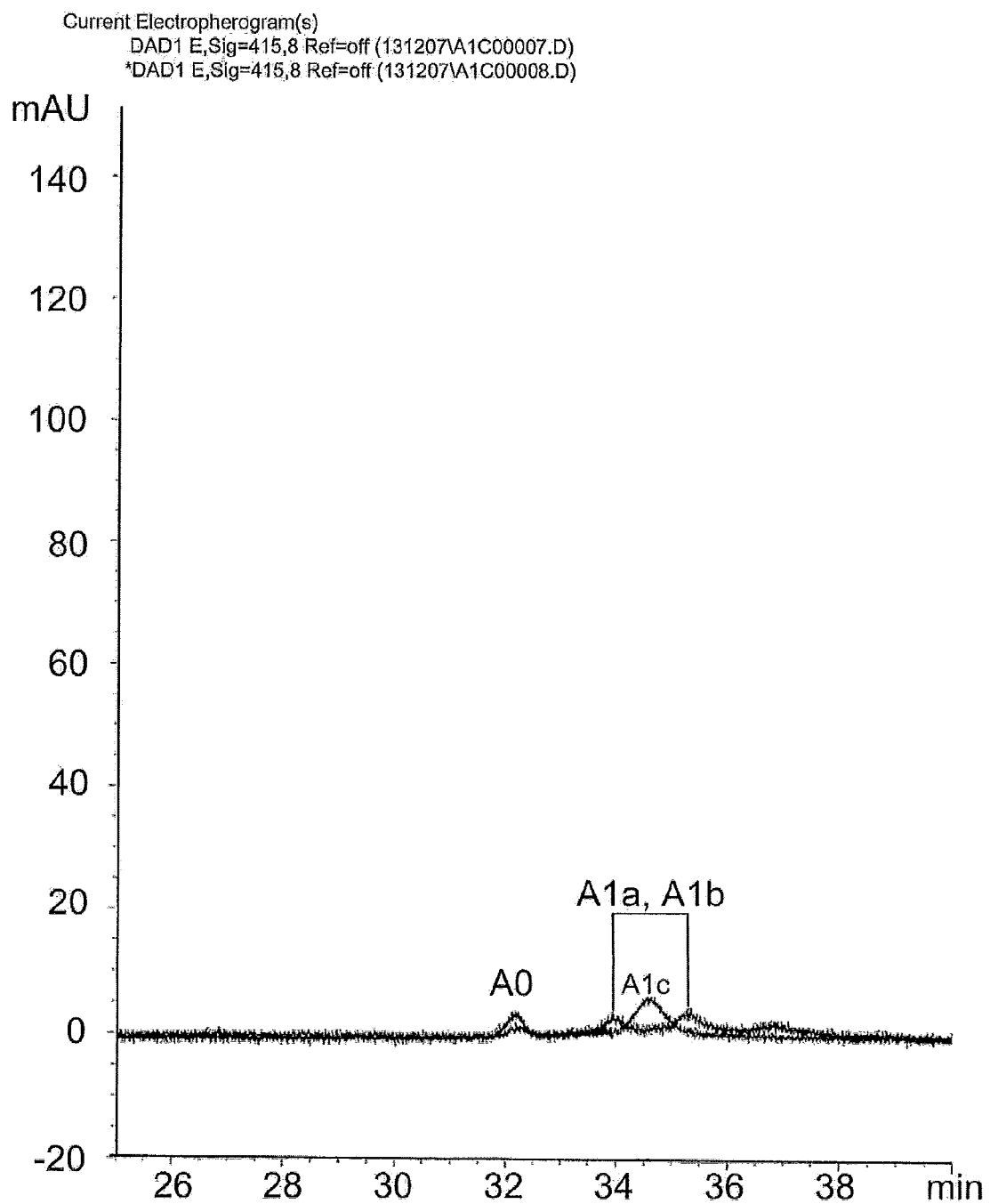
FIG. 5: standard electrophoretic profiles for $A_{1a,b}$ and $A_{1c}$ obtained on CE Agilent from reference samples containing different purified fractions of glycated haemoglobin, using a buffer composition containing 200 mM of CAPSO, 10 mM of putrescine and 50 mM of 3-carboxyphenylboronic acid (pH: 10.20; temperature: 24° C.; voltage: 6.1 kV, i.e. 190 V/cm; injection: 50 mbars 20 s).

Capillary electrophoresis was carried out from reference samples (Exocell, USA), containing different purified fractions of glycated haemoglobin (fractions $A_0$ and $A_{1c}$ or fractions $A_0$, $A_{1b}$ and $A_{1a}$), using a buffer composition containing 200 mM of CAPSO, 10 mM of putrescine and 50 mM of 3-carboxyphenylboronic acid (pH 10.20). The standard electrophoretic profiles for $A_{1a,b}$ and $A_{1c}$ obtained are presented in FIG. 5. The peak corresponding to $HbA_{1c}$ lies between the peaks corresponding to $HbA_{1b}$ and $HbA_{1a}$.

Example 6

Figure 6:
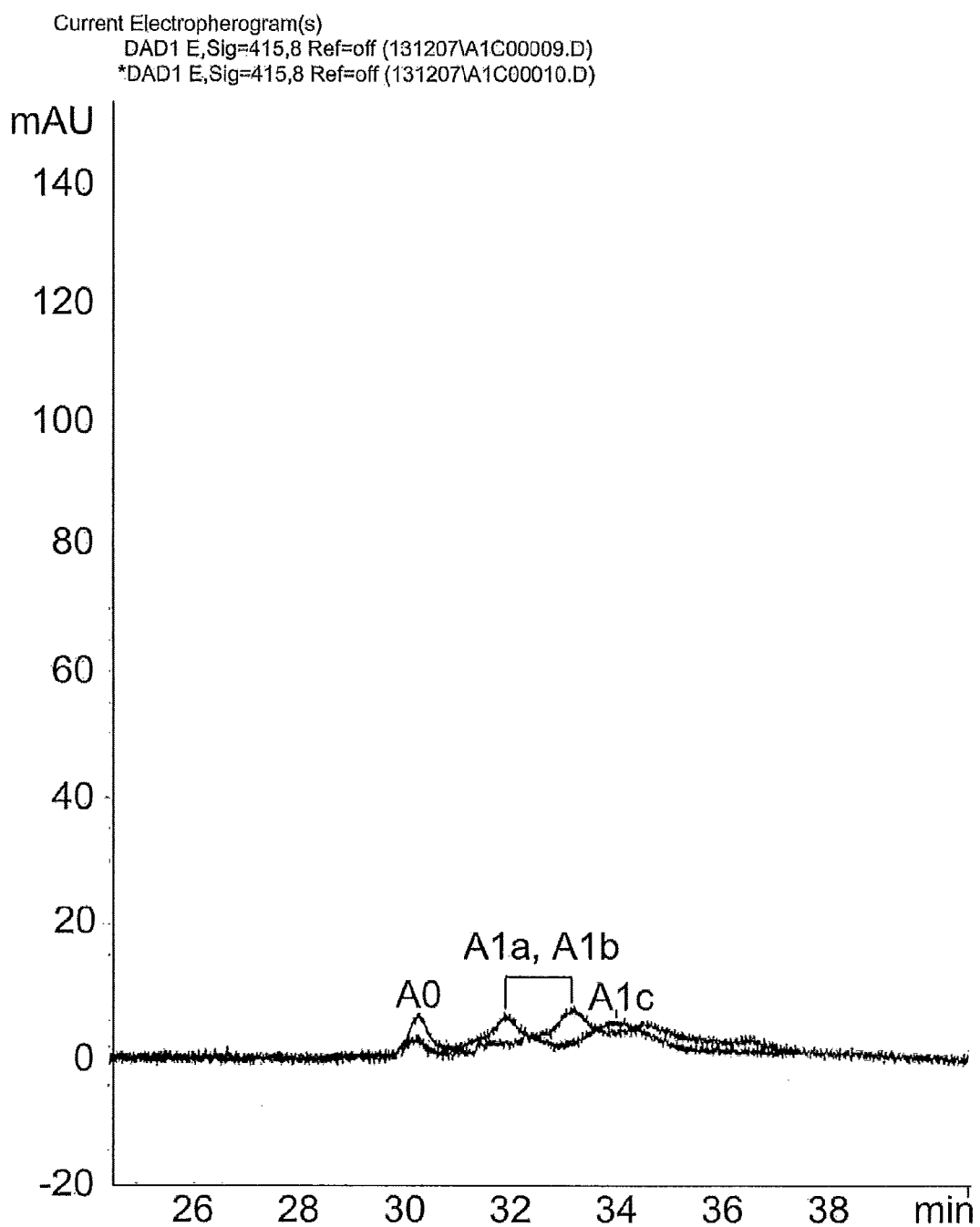
FIG. 6: standard electrophoretic profiles for $A_{1a,b}$ and $A_{1c}$ obtained on CE Agilent from reference samples containing different purified fractions of glycated haemoglobin, using a buffer composition containing 200 mM of CAPSO, 10 mM of putrescine and 50 mM of 3,5-dicarboxyphenylboronic acid (pH: 10.20; temperature: 24° C.; voltage: 6.1 kV, i.e. 190 V/cm; injection: 50 mbars 20 s).

Capillary electrophoresis was carried out from reference samples (Exocell, USA), containing different purified fractions of glycated haemoglobin (fractions $A_0$ and $A_{1c}$ or fractions $A_0$, $A_{1b}$ and $A_{1a}$), using a buffer composition containing 200 mM of CAPSO, 10 mM de DAB and 50 mM of 3,5-dicarboxyphenylboronic acid (pH 10.20). The standard electrophoretic profiles for $A_{1a,b}$ and $A_{1c}$ obtained are presented in FIG. 6. The peak corresponding to $HbA_{1c}$ lies after the peaks corresponding to $HbA_{1b}$ and $HbA_{1a}$.

Example 7

Figure 7:
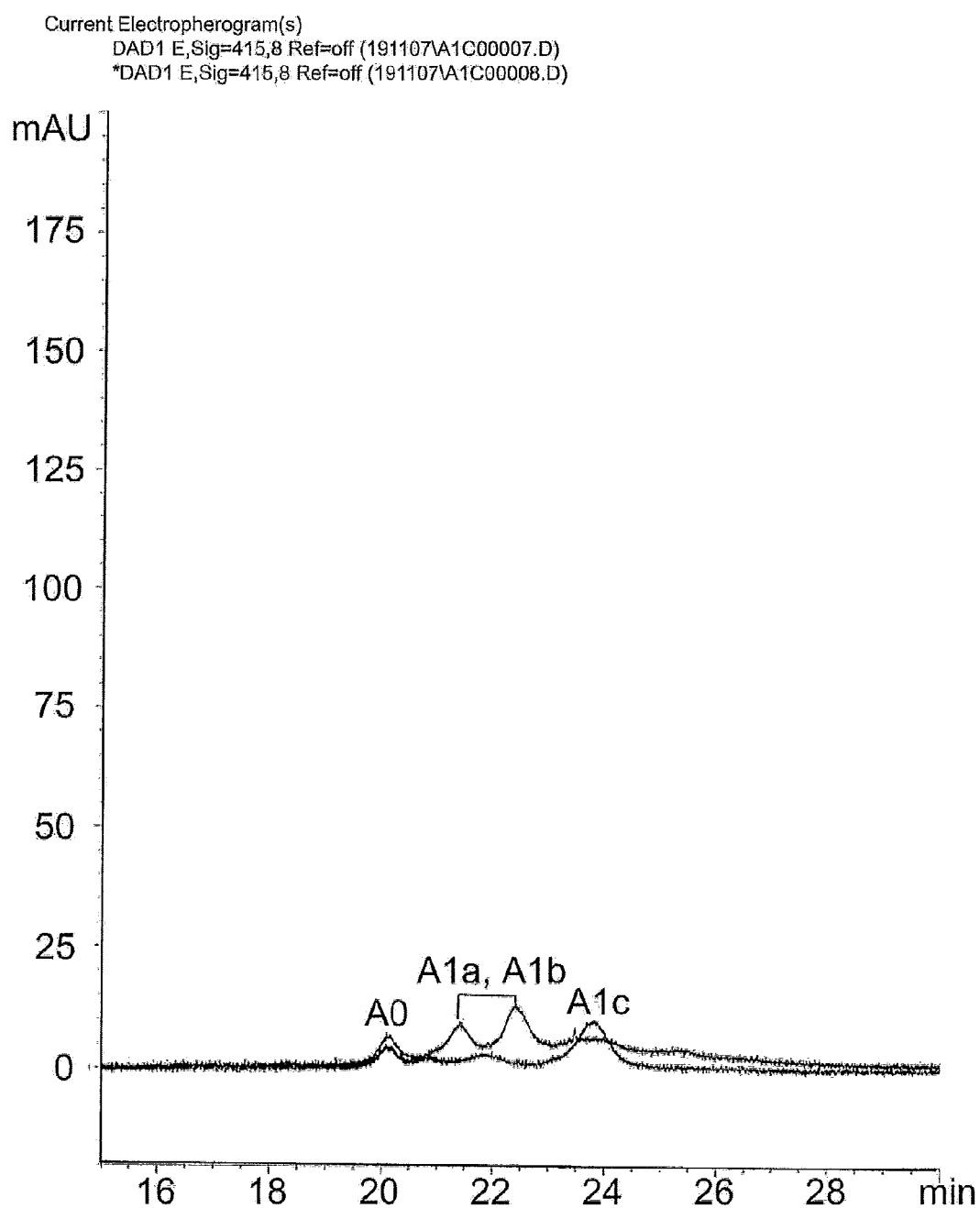
FIG. 7: standard electrophoretic profiles for $A_{1a,b}$ and $A_{1c}$ obtained on CE Agilent from reference samples containing different purified fractions of glycated haemoglobin, using a buffer composition containing 200 mM of CAPSO, 15 mM of putrescine and 100 mM of 3,5-dicarboxyphenylboronic acid (pH: 10.20; temperature: 30° C.; voltage: 10 kV, i.e. 310 V/cm; injection: 50 mbars 20 s).

Capillary electrophoresis was carried out from reference samples (Exocell, USA) containing different purified fractions of glycated haemoglobin (fractions $A_0$ and $A_{1c}$ or fractions $A_0$, $A_{1b}$ and $A_{1a}$), using a buffer composition containing 200 mM of CAPSO, 15 mM of flow retardant (putrescine) and 100 mM of 3,5-dicarboxyphenylboronic acid (pH 10.20). The standard electrophoretic profiles for $A_{1a,b}$ and $A_{1c}$ obtained are presented in FIG. 7. The peak corresponding to $HbA_{1c}$ lies after the peaks corresponding to $HbA_{1b}$ and $HbA_{1a}$ and is distinct from these peaks; the separation between the haemoglobin $HbA_{1c}$ and the haemoglobins $HbA_{1a}$ and $HbA_{1b}$ is excellent.

Example 8

Figure 8:
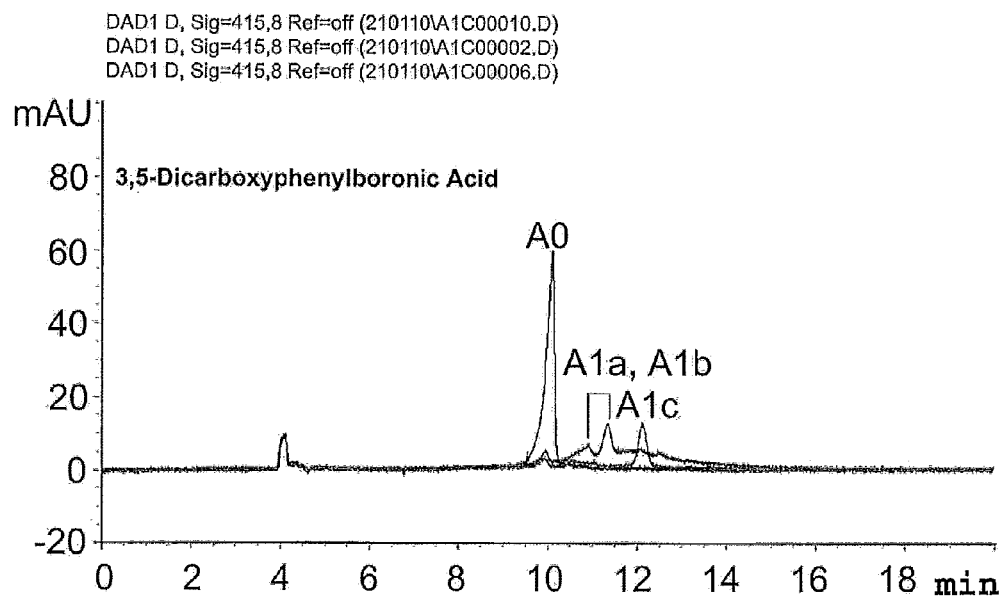
FIG. 8: standard electrophoretic profiles $A_0$, $A_{1a,b}$ and $A_{1c}$ obtained on CE Agilent from reference samples containing $HbA_0$ and/or different purified fractions of glycated haemoglobin, using a buffer composition containing 200 mM of CHES, 20 mM of putrescine and 30 mM of 3,5-dicarboxyphenylboronic acid at a pH of 9.40. Fused silica capillary, uncoated (temperature: 34° C.; voltage: 17.3 kV i.e. 520 V/cm; injection 50 mbars 20 s).

Capillary electrophoresis was carried out from reference samples containing $HbA_0$ and/or different purified fractions of glycated haemoglobin (fractions $A_0$ and $A_{1c}$ or fractions $A_0$, $A_{1b}$ and $A_{1a}$), using a buffer composition containing 200 mM of CHES, 20 mM of flow retardant (putrescine) and 30 mM of 3,5-dicarboxyphenylboronic acid (at a pH of 9.40). The standard electrophoretic profiles $A_0$, $A_{1a,b}$ and $A_{1c}$ obtained are presented in FIG. 8. The peak corresponding to $HbA_{1c}$ lies after the peaks corresponding to $HbA_0$, $HbA_{1b}$ and $HbA_{1a}$ and is clearly distinct from these peaks; the separation between the haemoglobin $HbA_{1c}$ and the $HbA_{1a}$ and $HbA_{1b}$ haemoglobins is excellent.

Example 9

Figure 9:
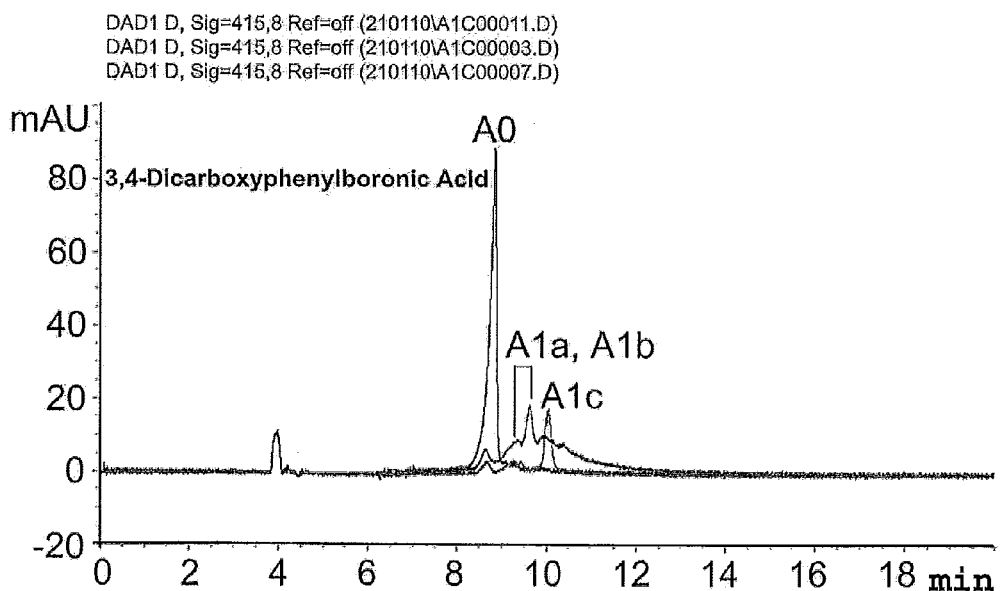
FIG. 9: standard electrophoretic profiles $A_0$, $A_{1a,b}$ and $A_{1c}$ obtained on CE Agilent from reference samples containing $HbA_0$ and/or different purified fractions of glycated haemoglobin, using a buffer composition containing 200 mM of CHES, 20 mM of putrescine and 30 mM of 3,4-dicarboxyphenylboronic acid at a pH of 9.40. Fused silica capillary, uncoated (temperature: 34° C.; voltage: 17.3 kV i.e. 520 V/cm; injection 50 mbars 20 s).

Capillary electrophoresis was carried out from reference samples containing $HbA_0$ and/or different purified fractions of glycated haemoglobin (fractions $A_0$ and $A_{1c}$ or fractions $A_0$, $A_{1b}$ and $A_{1a}$), using a buffer composition containing 200 mM of CHES, 20 mM of flow retardant (putrescine) and 30 mM of acid 3,4-dicarboxyphenylboronic (at a pH of 9.40). The standard electrophoretic profiles $A_0$, $A_{1a,b}$ and $A_{1c}$ obtained are presented in FIG. 9. It will be seen that the peak corresponding to $HbA_{1c}$ lies after the peaks corresponding to $HbA_0$, $HbA_{1b}$ and $HbA_{1a}$ and is clearly distinct from these peaks, the separation between the haemoglobin $HbA_{1c}$ and the $HbA_{1a}$ and $HbA_{1b}$ haemoglobins is excellent.

By comparing the electrophoretic profiles of examples 8 and 9, it will be seen that 3,5-dicarboxyphenylboronic acid can produce a slightly better result in terms of separation of $HbA_{1c}$ compared with the other fractions, while 3,4-dicarboxyphenylboronic acid allowed a slightly better result to be obtained in terms of focussing.

Example 10

Figure 10:
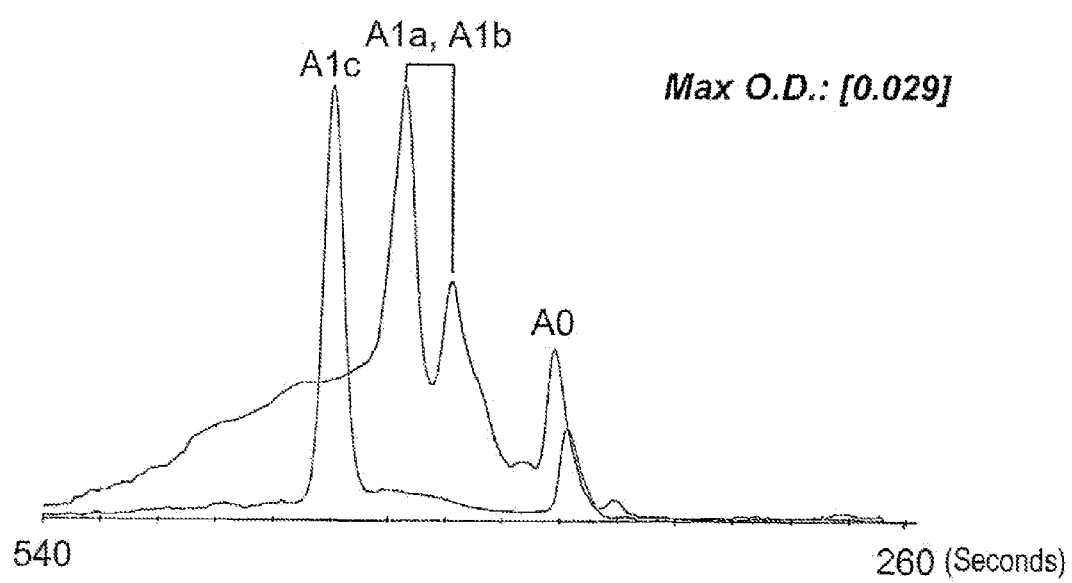
FIG. 10: standard electrophoretic profiles for $A_{1a,b}$ and $A_{1c}$ obtained on Capillaries® (Sebia) from reference samples containing different purified fractions of glycated haemoglobin, using a buffer composition containing 200 mM of CHES buffer, 20 mM of putrescine and 30 mM of 3,5-dicarboxyphenylboronic acid, at a pH of 9.40. Fused silica capillary, uncoated (temperature: 34° C.; voltage: 9.4 kV, i.e. 520 V/cm; injection 20 mbars 6 s).

Capillary electrophoresis was carried out on Capillaries® (Sebia) from reference samples (Exocell, USA) containing different purified fractions of glycated haemoglobin (fractions $A_0$ and $A_{1c}$ or fractions $A_0$, $A_{1b}$ and $A_{1a}$), using a buffer composition containing 200 mM of CHES buffer, 20 mM of putrescine and 30 mM of 3,5-dicarboxyphenylboronic acid, at a pH of 9.40. The standard electrophoretic profiles for $A1_{a,b}$ and $A_{1c}$ obtained are presented in FIG. 10. It will be seen that the peak corresponding to $HbA_{1c}$ lies after the peaks corresponding to $HbA_{1b}$ and $HbA_{1a}$ and is clearly distinct from these peaks; the separation between the haemoglobin $HbA_{1c}$ and the $HbA_{1a}$ and $HbA_{1b}$ haemoglobins is excellent.

Example 11

Figure 11:
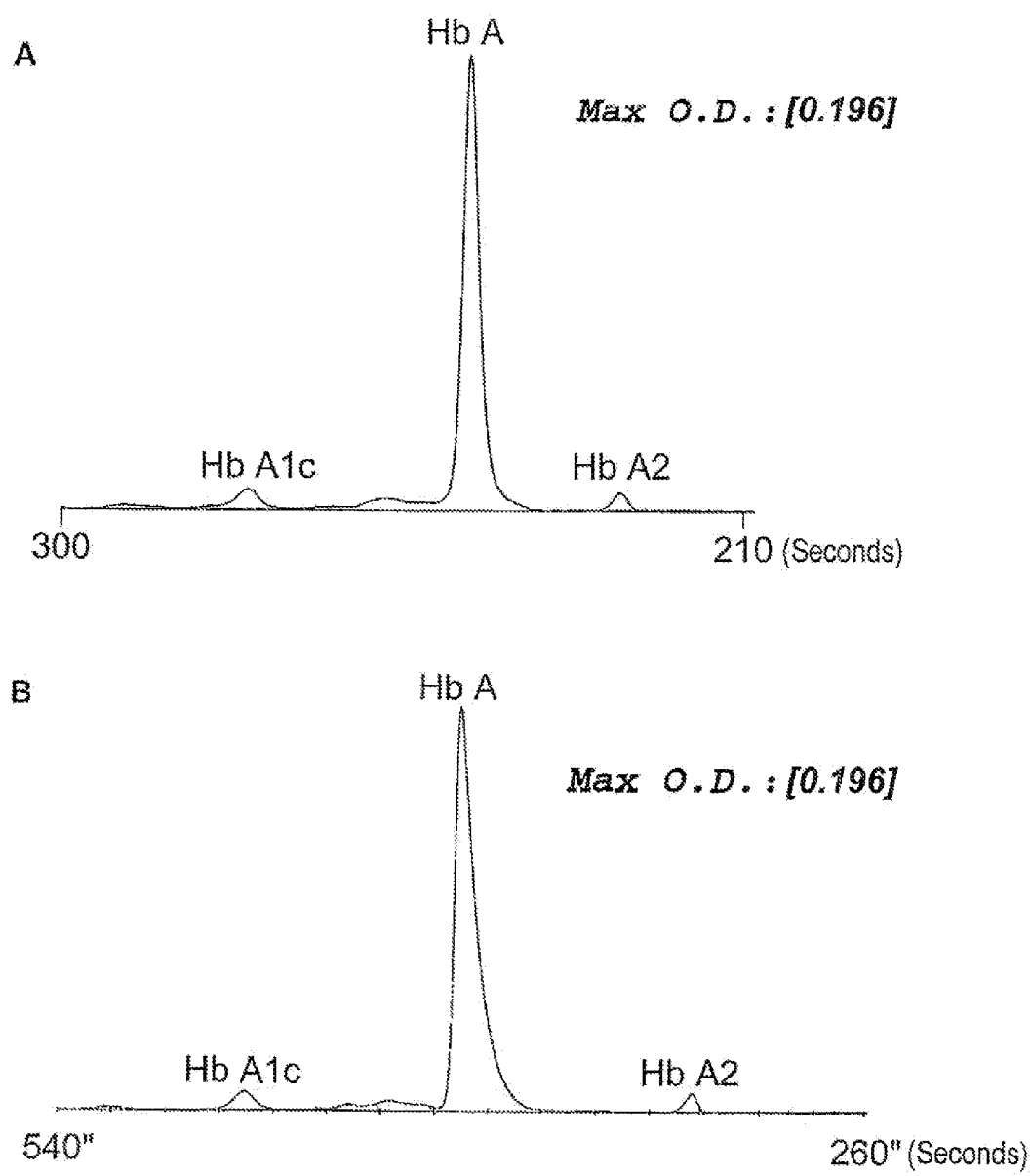
FIG. 11: electropherogram obtained on Capillaries® (Sebia) from a normal human blood sample diluted to 1/6th in the haemolyzing solution (water+1 g/L de Triton X100), using a buffer composition containing (A) 200 mM of CAPSO buffer, 10 mM of putrescine and 50 mM of 3,5-dicarboxyphenylboronic acid at a pH of 10.2, or (B) 200 mM of CHES buffer, 20 mM of putrescine and 30 mM of 3,5-dicarboxyphenylboronic acid, at a pH of 9.40. Fused silica capillary, uncoated (temperature: 34° C.; voltage: 9.4 kV, i.e. 520 V/cm; injection 8 mbars 6 s).

Analyses by capillary electrophoresis were carried out on normal human blood diluted to ⅙th in haemolyzing solution (water+1 g/L de Triton X100), using a buffer composition containing either 200 mM of CAPSO buffer, 10 mM of putrescine and 50 mM of 3,5-dicarboxyphenylboronic acid, at a pH of 10.20, or 200 mM of CHES buffer, 20 mM of putrescine and 30 mM of 3,5-dicarboxyphenylboronic acid, at a pH of 9.40. The electropherograms obtained on Capillaries® (Sebia) using a fused silica capillary, uncoated, are presented in FIGS. 11A and 11B respectively. In both cases, complete separation of the haemoglobin $HbA_{1c}$ from the other haemoglobins forms is observed.

Example 12

Figure 12:
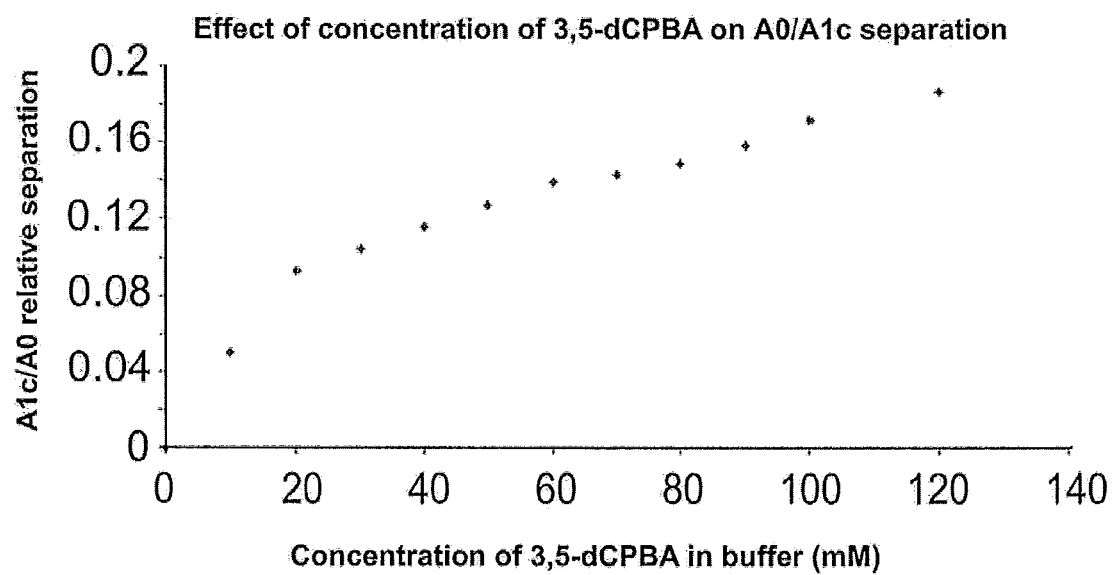
FIG. 12: study of the influence of the concentration of 3,5-dicarboxyphenylboronic acid in the buffer composition on the separation between $A_{1c}$ and $A_o$ haemoglobins (temperature: 30° C.; voltage: 10 kV, i.e. 310 V/cm).

The influence of concentration of 3,5-dicarboxyphenylboronic acid in the buffer composition on the separation between the $A_{1c}$ and $A_o$ haemoglobins was studied. The buffer composition used contained 200 mM of CAPSO, 15 mM of putrescine and 0 to 120 mM of 3,5-dicarboxyphenylboronic acid. The results are presented in FIG. 12. The $A_{1c}/A_o$ separation increased with the concentration of 3,5-dicarboxyphenylboronic acid.

Example 13

Figure 13:
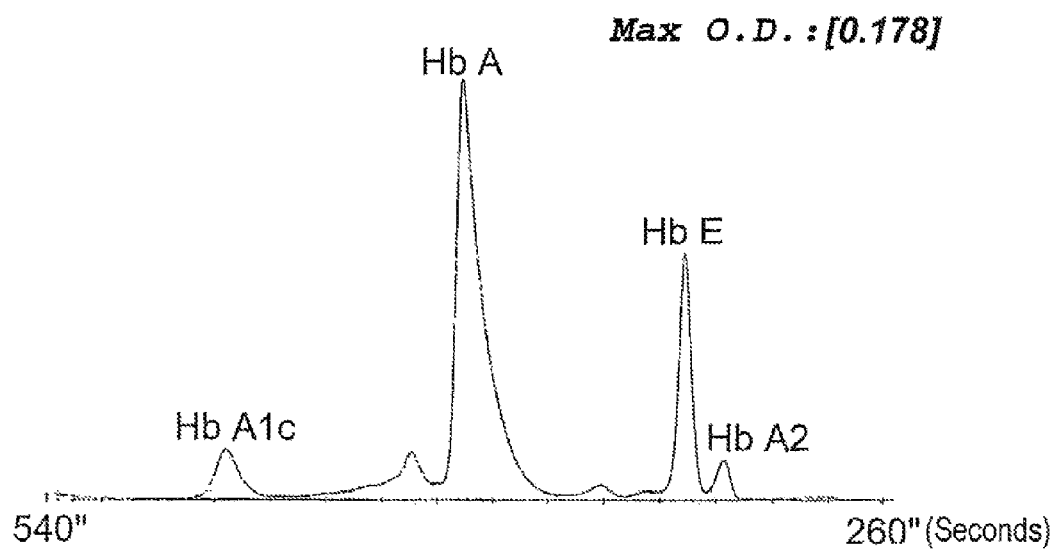
FIG. 13: electropherogram obtained on Capillaries® (Sebia) from a normal human blood sample comprising a variant HbE, diluted to $1/6^{th}$ in the haemolyzing solution (water+1 g/L de Triton X100), using a buffer composition containing 200 mM of CHES buffer, 20 mM of putrescine and 30 mM of 3,5-dicarboxyphenylboronic acid, at a pH of 9.40, and a fused silica capillary, uncoated (temperature: 34° C.; voltage: 9.4 kV, i.e. 520 V/cm; injection 8 mbars 6 s).
Figure 14:
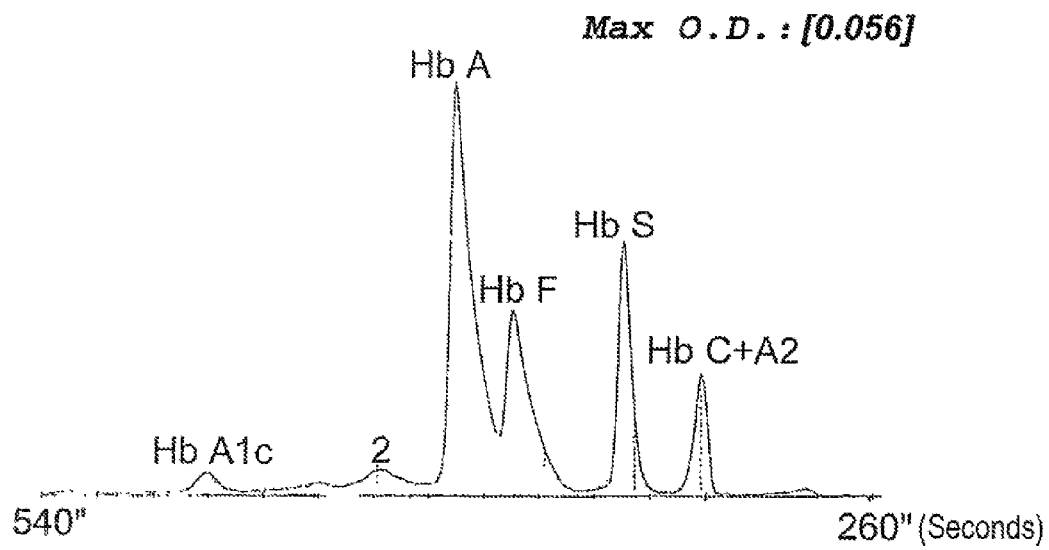
FIG. 14: electropherogram obtained on Capillaries® (Sebia) from a control AFSC diluted to $1/6^{th}$ in the haemolyzing solution (water+1 g/L de Triton X100), using a buffer composition containing 200 mM of CHES buffer, 20 mM of putrescine and 30 mM of 3,5-dicarboxyphenylboronic acid, at a pH of 9.40, and a fused silica capillary, uncoated (temperature: 34° C.; voltage: 9.4 kV, i.e. 520 V/cm; injection 8 mbars 6 s).
Figure 15:
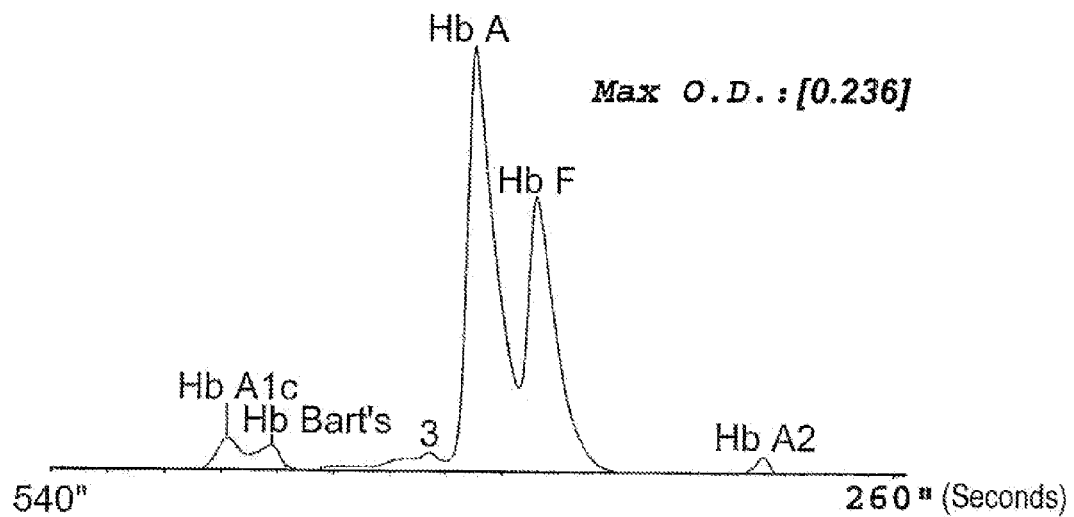
FIG. 15: electropherogram obtained on Capillaries® (Sebia) from a pool of normal blood comprising F and Bart's variants, diluted to $1/6^{th}$ in the haemolyzing solution (water+1 g/L de Triton X100), using a buffer composition containing 200 mM of CHES buffer, 20 mM of putrescine and 30 mM of 3,5-dicarboxyphenylboronic acid, at a pH of 9.40, and a fused silica capillary, uncoated (temperature: 34° C.; voltage: 9.4 kV, i.e. 520 V/cm; injection 8 mbars 6 s).
Figure 16:
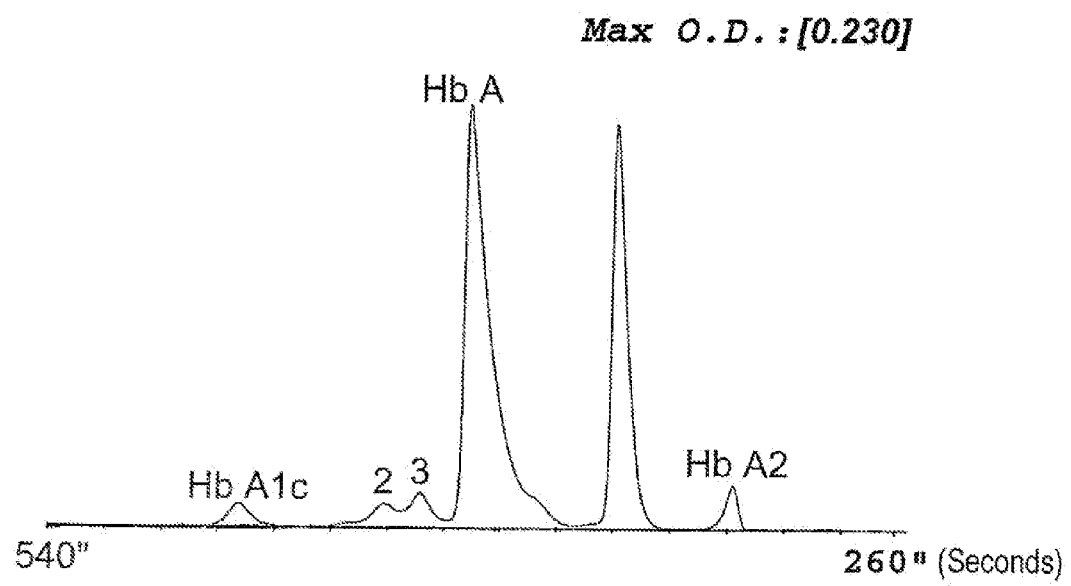
FIG. 16: electropherogram obtained on Capillaries® (Sebia) from a normal human blood sample comprising a HbD variant, diluted to $1/6^{th}$ in the haemolyzing solution (water+1 g/L de Triton X100), using a buffer composition containing 200 mM of CHES buffer, 20 mM of putrescine and 30 mM of 3,5-dicarboxyphenylboronic acid, at a pH of 9.40, and a fused silica capillary, uncoated (temperature: 34° C.; voltage: 9.4 kV, i.e. 520 V/cm; injection 8 mbars 6 s).

Capillary electrophoreses were carried out on Capillaries® (Sebia) using four different samples diluted by ⅙th in the haemolyzing solution (water+1 g/L de Triton X100): normal human blood comprising a HbE variant (FIG. 13), a AFSC control (FIG. 14), a pool of normal blood comprising F and Bart's variants (FIG. 15) and normal human blood comprising a HbD variant (FIG. 16). Capillary electrophoresis was carried out in a buffer composition containing 200 mM of CHES buffer, 20 mM of putrescine and 30 mM of 3,5-dicarboxyphenylboronic acid, at a pH of 9.40, using a fused silica capillary, uncoated.

FIGS. 13-16 show the absence of interference from the principal variants of haemoglobin (E, F, S, C, D and Bart) with the $HbA_{1c}$ fraction. Note, however, that in the case of Bart's haemoglobin, the resolution is not complete between the Hb Bart and $HbA_{1c}$ fractions. As a consequence, in order to be able to assay $HbA_{1c}$ in the presence of Hb Bart, these two fractions should be capable of being quantified using a suitable integration method. If this is not possible, it will be necessary to alert the user to this, in case he observed this type of profile with a shoulder on the expected peak.

Example 14

The results obtained by capillary electrophoresis by the method of invention using the Capillaries® (Sebia) analyzer were compared with the results obtained with one of the reference techniques: HPLC with the Variant II Turbo® (Bio-Rad).analyzer.

Capillary electrophoresis was carried out from whole blood diluted to ⅙th in the haemolyzing solution (water+1 g/L de Triton X100), in a buffer composition containing 200 mM of CHES buffer, 20 mM of putrescine and 30 mM of 3,5-dicarboxyphenylboronic acid, at a pH of 9.40.

Figure 17:
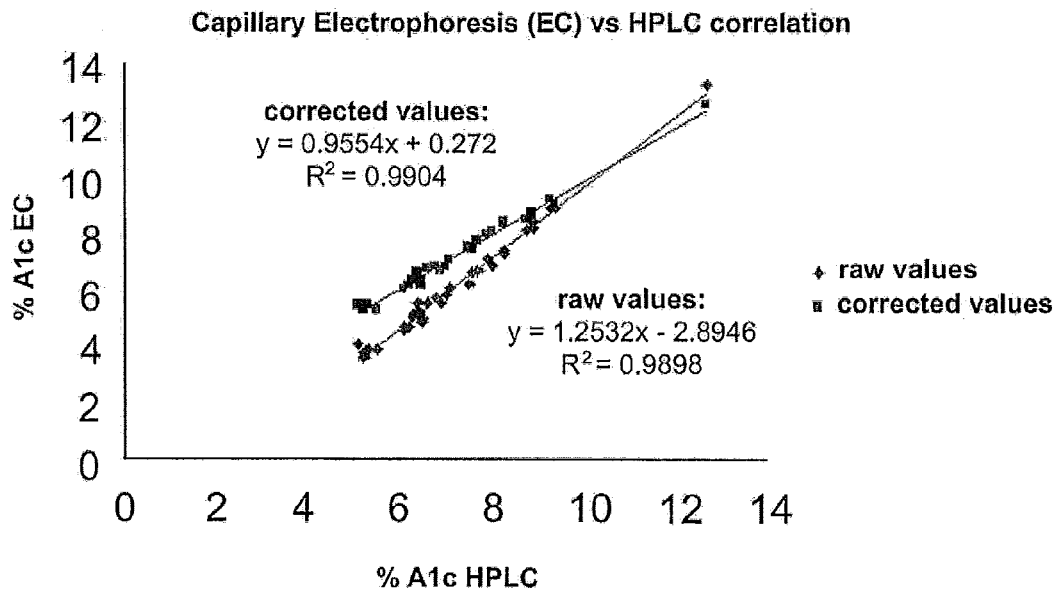
FIG. 17: comparison of the results obtained by the inventors by capillary electrophoresis using the Capillaries® (Sebia) analyzer with the results obtained by HPLC with the Variant II Turbo® (Bio-Rad) analyzer.

FIG. 17 shows the very good correlation of this novel technique for analysis by capillary electrophoresis with the analysis of $HbA_{1c}$ by HPLC with the Variant II turbo® from Bio-Rad. After calibration of the EC data using 2 calibrators (weak $A1_c$ and strong $A1_c$), the values obtained by the method of invention were very close to those obtained by the reference method.

Example 15

Study demonstrating the absence of interference of the labile fraction of $HbA_{1c}$ with the assay of $HbA_{1c}$ using the method of the invention.

Hypothesizing that the compound complexing glucose and providing negative charges at an alkaline pH used in the context of the analysis method of the invention would be capable of interacting with blood glucose (this interaction is hypothetical and has not been demonstrated), a study of any interference of free glucose on the result of the blood of $HbA_{1c}$ was carried out as follows: normal blood was incubated for 3 hours at 37° C. with different concentrations of glucose (0 to 50 g/L) in order to create the labile form of $HbA_{1c}$ (form obtained before rearrangement of the molecule (Amadori rearrangement)). Once incubation had been carried out, the blood samples were centrifuged and the pellets obtained were reconstituted in physiological water and the haemolyzing solution (15 µL of pellet+25 µL physiological water+160 µL of haemolyzing solution (water+1 g/L Triton X100)) was then analyzed in parallel using a Hydrasys® automated machine from Sebia ($HbA_{1c}$ gel) and using the Capillaries® (Sebia) technique, using a buffer composition containing 200 mM of CHES buffer, 20 mM of putrescine and 30 mM of 3,5-dicarboxyphenylboronic acid, at a pH of 9.40.

The HbA1c gel obtained by the analysis on the Hydrasys® automated machine (see FIG. 18A) confirmed the formation of labile fraction of the HbA1c migrating to the same level as the HbA1c and in an increasing concentration as the concentration of glucose increased during incubation with the blood. It should be noted that in gel, under the normal conditions of use defined by Sebia, the labile fraction did not appear, in particular because of the acid pH of the haemolyzing solution.

Figures 18A, 18C:
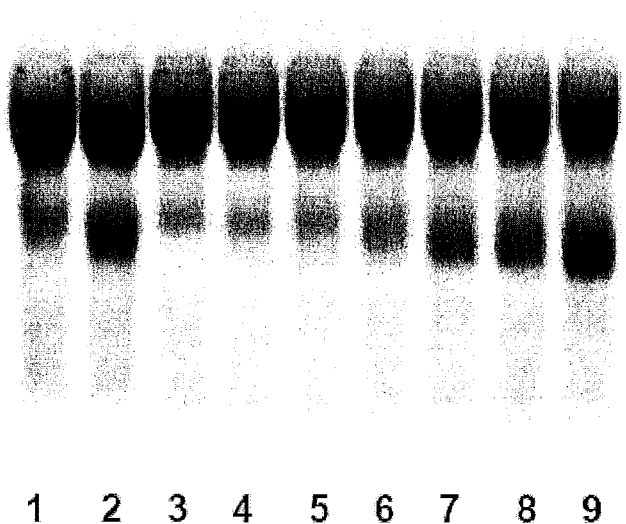
FIG. 18A: agarose gel of $HbA_{1c}$ carried out on Hydrasys® (Sebia) automated machine. Tracks 1 and 2: weak (5.0%) $A_{1c}$ calibrator and strong (10.8%) $A_{1c}$ calibrator. Tracks 3 to 9: normal whole blood incubated for 3 h at 37° C. with glucose at a concentration of 0 g/L (reference; track 3), 1 g/L (track 4), 5 g/L (track 5), 10 g/L (track 6), 20 g/L (track 7), 30 g/L (track 8) and 50 g/L (track 9).
FIG. 18C: table summarizing values for $HbA_{1c}$ obtained on agarose gel and with the Capillaries® (Sebia) analyzer for the analyses of the blood presented in FIGS. 18A and 18B.
Figure 18B:
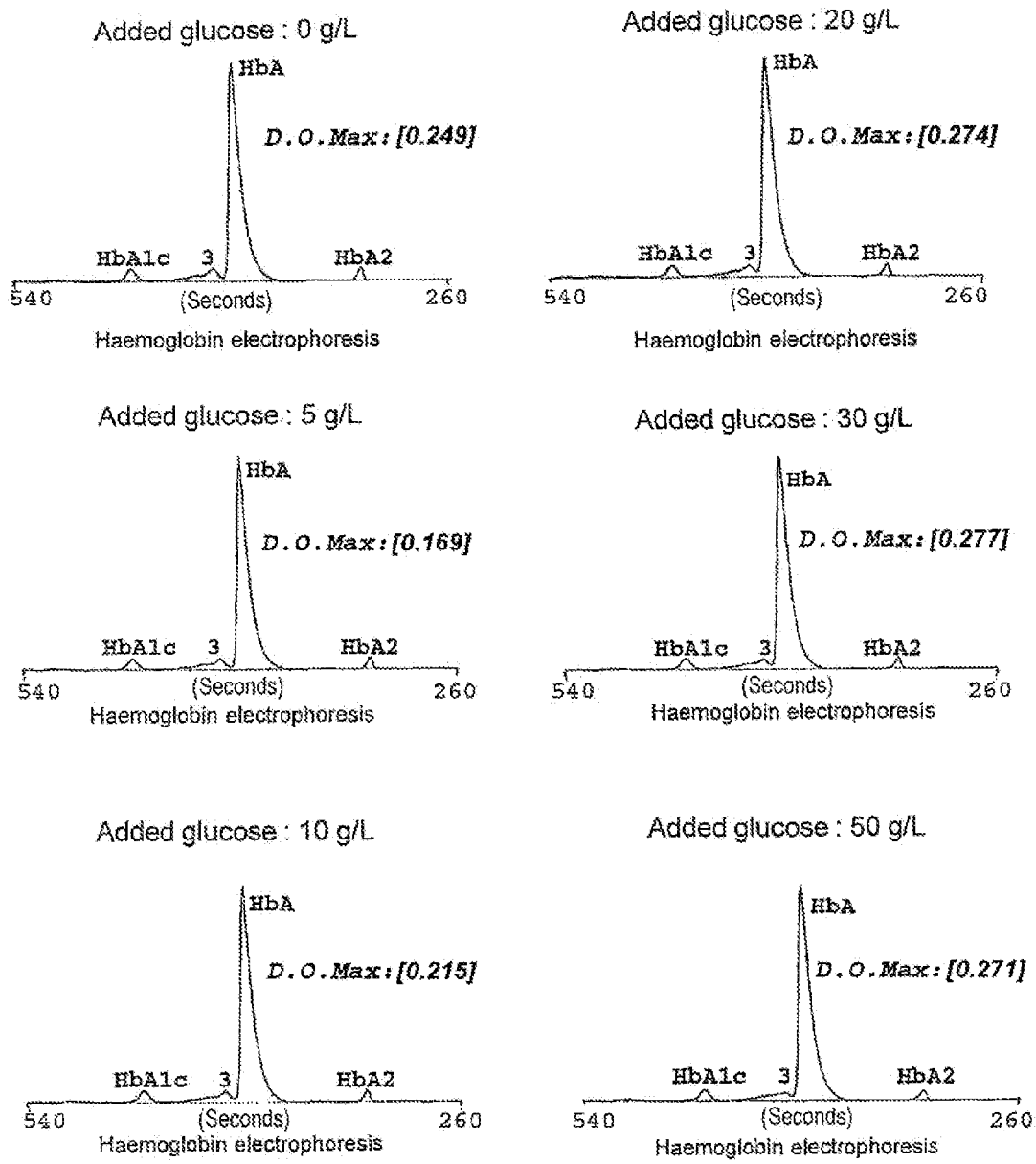
FIG. 18B: capillary electrophoresis profiles obtained with the Capillaries® (Sebia) analyzer with the samples of FIG. 18A. The analysis was not, however, carried out for the sample containing 1 g/L of glucose as there was no visible difference in the gel (FIG. 18A). The samples were diluted to $1/6^{th}$ in the haemolyzing solution (water+1 g/L de Triton X100), using a buffer composition containing 200 mM of CHES buffer, 20 mM of putrescine and 30 mM of 3,5-dicarboxyphenylboronic acid, at a pH of 9.40, and a fused silica capillary, uncoated (temperature: 34° C.; voltage: 9.4 kV, i.e. 520 V/cm; injection 8 mbars 6 s).

In contrast, the analyses carried out on Capillaries® (Sebia) with a buffer composition of the invention (200 mM of CHES buffer, 20 mM of putrescine and 30 mM of 3,5-dicarboxyphenylboronic acid, at a pH of 9.40), on the same blood samples showed that the assay was not perturbed by the presence of free glucose, regardless of the concentration of incubated glucose, in the range studied (0 to 50 g/L): the profiles and the values of HbA1c were unchanged (see FIGS. 18B and 18C).

REFERENCES

Abraham, E. C.; Cameron, B. F.; Abraham, A.; Stallings, M., "Glycosylated hemoglobins in heterozygotes and homozygotes for hemoglobin C with or without diabetes", Journal of Laboratory and Clinical Medicine, 104, 602-609, 1984.

Beccaria, L.; Chiumello, G.; Gianazza, E.; Luppis, B.; Righetti, P G., "Hemoglobin $A_{1c}$ separation by isoelectric focusing'", American Journal of Hematology, 4, 367-374, 1978.

Bosisio, A.; Righetti, P., "Determination of glycated haemoglobin by isoelectric focusing in non-linear pH gradients", Journal of Chromatography, 307, 103-110, 1984.

Doelman, C; Siebelder, C; Nijhof, W.; Weykamp, W.; Janssens, J.; Penders, T., "Capillary electrophoresis system for hemoglobin $A_{1c}$ determinations evaluated", Clinical Chemistry, 43, 4, 644-648, 1997.

Hempe, J M.; Craver, R D., "Quantification of hemoglobin variants by capillary isoelectric focusing",Clinical Chemistry, 40,12, 2288-2295, 1994.

Hempe, J M.; Granger, J N.; Craver, R D., "Capillary isoelectric focusing of hemoglobin variants in the pediatric clinical laboratory", Electrophoresis, 18, 1785-1795, 1997.

Janssens, J., "Capillary electrophoresis detection and/or analysis method and unit", EP 0 733 900 A2, 1996.

Janssens, J.; Chevigne, P.; Louis, P., "Capillary electrophoresis method using initialized capillary and polyanion-containing buffer and chemical kit therefore", U.S. Pat. No. 5,611,903, 1997.

Menard, L; Dempsey, M.; Blankstein, L; Aleyassine, H.; Wacks, M,; Soeldner, J., "Quantitative determination of glycosylated hemoglobin A1 by agar gel electrophoresis", Clinical Chemistry, 26, 11, 1598-1602,1980.

Molteni, S.; Frischknecht, H.; Thormann, W., "Application of dynamic capillary isoelectric focusing to the analysis of human hemoglobin variants", Electrophoresis, 15, 22-30, 1994.

Panteghini, M. John, W. G., on behalf of the IFCC Scientific Division, "Implementation of haemoglobin $A_{1c}$ results traceable to the IFCC reference system: the way forward.", Clin Chem Lab Med., 45(8), 942-4, 2007.

Simon, M.; Cuan J., "Hemoglobin Aie by isoelectric focusing", Clinical Chemistry, 28,1, 9-12, 1982.

Siren, H.; Laitinen, P.; Turpeinen, U.; Karppinen, P., "Direct monitoring of glycohemoglobin $A_{1c}$ in the blood samples of diabetic patients by capillary electrophoresis. Comparison with an immunoassay method", Journal of Chromatography A, 979, 201-207, 2002.

Stickland, M.; Perkins, C; Wales, J, "The measurement of haemoglobin $A_{1c}$ by isolectric focusing in diabetic patients", Diabetologia, 22, 315-317,1982.

Wilson, D. H., Bogacz, J. P., Forsythe, C. M., Turk, P. J., Lane, T. L., Gates, R. C., Brandt, D. R. "Fully automated assay of glycohemoglobin with the Abbott IMx analyzer: novel approaches for separation and detection", Clin Chem., 39(10), 2090-7, 1993.

The invention claimed is:

1. A method for analysis by capillary electrophoresis of one or several glycated haemoglobin(s) comprising at least one globin chain comprising a glucose residue bound to the amino acid in the N-terminal position of the beta globin chain, contained in a biological sample comprising haemoglobins, said method comprising the following steps a. introducing a buffer composition and a biological sample into an electrophoresis capillary, said buffer composition comprising at least one compound which specifically complexes the glucose residue(s) bound to an amino acid in the N-terminal position in glycated haemoglobins of the biological sample and provides said glycated haemoglobin(s) with several negative electric charges at an alkaline pH,wherein said compound which specifically complexes the glucose residue(s) of glycated haemoglobins of the biological sample and provides negatice charges at an alkaline pH comprises two or more than two functional groups, at least one of said functional groups specifically complexing one or more glucose residue(s), thereby providing one negative electric charge per complexed glucose residue,and at least one off said functional groups does not complex the glucose residue(s) thereby providing each glucose residue with one or more additional negative charges at an alkaline pH and is:
   (i) a boronate compound with general formulaI RB(OH)$_2$ or RB(OH)$_3$, in which the group R comprises at least one arvl and/or alkyl (linear,branched or cyclic) and/or an aralkyl and/or other functional groups or heteroatoms, and/or a combination thereof, and said group R provides glycated hamoglobins with one or several negative electric charge(s) at an alkaline pH for each glucose residue complexed with the boronate group; wherein said boronate compound is a dicaroxyphenylboronic acid or
   (ii) a salt of a dicarboxyphenylboronic acid;
b. performing capillary electrophoresis on the buffered biological sample to separate constituents of the biological sample; and
c. detecting one or several haemoglobin(s) present in the biological sample.

2. A method according to claim 1, in which the concentration in the buffer composition of the compound which specifically complexes glucose residues of glycated haemoglobin(s) of the biological sample and provides negative charges at an alkaline pH is in stoechiometric excess with respect to the total quantity of proteins, compared with the total quantity of all of the haemoglobins present in the biological sample or compared with the total quantity of all of the haemoglobins comprising glucose present in the biological sample.

3. A method according to claim 1, in which the concentration in the buffer composition of the compound which specifically complexes glucose residues of glycated haemoglobins of the biological sample and provides negative charges at an alkaline pH is in the range 0.10 to 100 mM.

4. A method according to claim 1, in which the buffer composition further comprises a flow retardant.

5. A method according to claim 4, in which the concentration of flow retardant in the buffer composition is in the range 0.10 to 40 mM.

6. A method according to claim 1, in which the buffer composition further comprises:
   a buffer compound having a pKa in the range 8.0 to 11.0; and/or
   a base; and/or
   a salt,; and/or
   a diluting solution.

7. A method according to claim 6, in Which the buffer compound is a zwitterionic compound.

8. A method according to claim 6, in which the concentration of buffer compound in the buffer composition is in the range 20 to 500 mM.

9. A method according to claim 1, in which the buffer composition has a pH of 9 or more.

10. A method according to claim l, further comprising a step for generating an electropherogram from a detection signal which is proportional to the quantity of haemoglobin(s) detected.

11. A method according to claim 1, further comprising a step for determining the quantity of one or several haemoglobin(s) present in the biological sample and/or of the proportion of one or several haemoglobin(s) present in the biological sample with respect to the total quantity of proteins, the total quantity of haemoglobin or the quantity of certain haemoglobins present in the biological sample.

12. A method according to claim 1, further comprising a step for quantification of one or several haemoglobin(s) present in the biological sample compared with one or several standardized calibrator(s).

13. A method according to claim 1, in which the biological sample is a blood sample.

14. A method according to claim 1, in which the biological sample is diluted in a haemolyzing solution.

15. The method according to claim 1, wherein the boronate compound is a dicarboxphenylboronic acid selected from 3,4-dicarboxyphenylboronic acid and 3,5-dicarboxyphenylboronic acid.

* * * * *